(12) United States Patent
Duan et al.

(10) Patent No.: US 9,914,707 B2
(45) Date of Patent: Mar. 13, 2018

(54) NAPHTHYLAMIDE COMPOUND, PREPARATION METHOD AND USE THEREOF

(71) Applicant: SHANGHAI INSTITUTE OF MATERIA MEDICA, CHINESE ACADEMY OF SCIENCES, Shanghai (CN)

(72) Inventors: Wenhu Duan, Shanghai (CN); Jian Ding, Shanghai (CN); Yongcong Lv, Shanghai (CN); Hua Xie, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 15/120,771

(22) PCT Filed: Feb. 15, 2015

(86) PCT No.: PCT/CN2015/073121
§ 371 (c)(1),
(2) Date: Aug. 23, 2016

(87) PCT Pub. No.: WO2015/124101
PCT Pub. Date: Aug. 27, 2015

(65) Prior Publication Data
US 2017/0066723 A1    Mar. 9, 2017

(30) Foreign Application Priority Data

Feb. 24, 2014 (CN) .......................... 2014 1 0062209

(51) Int. Cl.
| | |
|---|---|
| C07D 231/56 | (2006.01) |
| C07D 261/20 | (2006.01) |
| C07D 413/12 | (2006.01) |
| C07D 401/12 | (2006.01) |
| C07D 491/048 | (2006.01) |
| C07D 495/04 | (2006.01) |

(52) U.S. Cl.
CPC ......... *C07D 231/56* (2013.01); *C07D 261/20* (2013.01); *C07D 401/12* (2013.01); *C07D 413/12* (2013.01); *C07D 491/048* (2013.01); *C07D 495/04* (2013.01)

(58) Field of Classification Search
CPC .. C07D 231/56; C07D 261/20; C07D 401/12; C07D 413/12; C07D 491/048; C07D 495/04
USPC ..................................................... 548/362.1
See application file for complete search history.

(56) References Cited

U.S. PATENT DOCUMENTS 5,006,519 A    4/1991   DiNinno et al.

FOREIGN PATENT DOCUMENTS

| CN | 101906076 A | 12/2010 |
|---|---|---|
| CN | 102470134 A | 5/2012 |
| CN | 103288728 A | 9/2013 |
| CN | 103351336 A | 10/2013 |
| CN | 103896836 A | 7/2014 |
| WO | 0002871 A1 | 1/2000 |
| WO | 2006039718 A2 | 4/2006 |
| WO | 2006059234 A2 | 6/2006 |
| WO | 2007005668 A2 | 1/2007 |
| WO | 2007031265 A2 | 3/2007 |
| WO | 103923004 A | 7/2014 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Lv et al., "Discovery of a New Series of Naphthamides as Potent VEGFR-2 Kinase Inhibitors", ACS Medicinal Chemistry Letters, vol. 5, No. 5, pp. 592-597 (Feb. 24, 2014).
Miduturu et al., "High-Throughput Kinase Profiling: A More Efficient Approach Toward the Discovery of New Kinase Inhibitors", Chemistry & Biology, vol. 18, No. 7, pp. 868-879 (Jul. 29, 2011).
Weiss et al., "Evaluation of a Series of Naphthamides as Potent, Orally Active Vascular Endothelial Growth Factor Receptor-2 Tyrosine Kinase Inhibitors", Journal of Medicinal Chemistry, vol. 51, No. 6, pp. 1668-1680 (Mar. 7, 2008)).
Liu, et al., "Synthesis and Biological Activities of Novel Nitrogen-Containing Hetercyclic Compounds", Doctoral Dissertations of Nanchang University, 120 pgs (Dec. 31, 2014).

(Continued)

*Primary Examiner* — Kristin Vajda
(74) *Attorney, Agent, or Firm* — Panitch Schwarze Belisario & NAdel LLP

(57) ABSTRACT

The present invention relates to a naphthylamide compound of the structure as represented by formula (I), medicinal salts, prodrugs and hydrates or solvates thereof, and also relates to a method of preparing the compounds, pharmaceutical compositions comprising the compounds and the uses thereof as protein tyrosine kinase inhibitors, particularly as VEGFR-2 inhibitors, in preparing drugs for preventing and treating diseases related to abnormal angiogenesis.

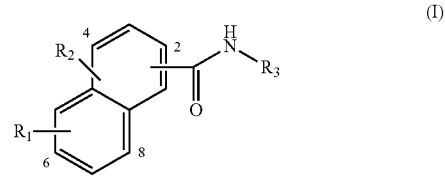

20 Claims, No Drawings

(56) References Cited

OTHER PUBLICATIONS

Dai, et al., "Discovery of N-(4-(3-Amino-1H-indazol-4-yl)phenyl)-N-(2-fluoro-5-methylphenyl)urea(ABT-869), a 3-Aminoindazole-Based Orally Active Multitargeted Receptor Tyrosine Kinase Inhibitor", Journal Med. Chem., vol. 50, pp. 1584-1597 (Mar. 8, 2007).

Mendel, et al., "In Vivo Antitumor Activity of SU11248, a Novel Tyrosine Kinase Inhibitor Targeting Vascular Endothelial Growth Factor and Platelet-derived Growth Factor Receptors: Determination of a Pharmacokinetic/Pharmacodynamic Relationship", Clinical Cancer Research, vol. 9, pp. 327-337 (Jan. 2003).

Shibuya, "Vascular Endothelial Growth Factor-Dependent and -independent Regulation of Angiogenesis", BMB Reports, pp. 278-286 (2008).

Int'l Search Report dated May 27, 2015 in Int'l Application No. PCT/CN2015/073121.

\* cited by examiner

NAPHTHYLAMIDE COMPOUND, PREPARATION METHOD AND USE THEREOF

CROSS REFERENCE TO RELATED APPLICATION

This application is a Section 371 of International Application No. PCT/CN2015/073121, filed Feb. 15,2015,which is published in the Chinese language on Aug. 27,2015, under International Publication No. WO 2015/124101 A1 and the disclosure of which is herein incorporated by reference in its entirety.

TECHNICAL FIELD

The present invention relates to the field of pharmaceutical chemistry and pharmacotherapeutics, particularly to naphthylamide compounds, medicinal salts, prodrugs and hydrates or solvates thereof, and also relates to a method of preparing the compounds, pharmaceutical compositions comprising the compounds and the uses thereof as protein tyrosine kinase inhibitors, particularly as VEGFR-2 inhibitors, in preparing drugs for preventing and treating diseases related to abnormal angiogenesis.

BACKGROUND ART

Angiogenesis (Angiogenesis), i.e., new blood vessel constructed from existing blood vessel, is an important mechanism of many physiological and pathological processes occurrence. Under normal circumstances, angiogenesis occurs only in embryonic development, wound healing and menstrual cycles of women. Abnormal angiogenesis may occur under pathological conditions (Shibuya M. *BMB. Rep.* 2008; 41(4): 278-86), especially during the growth of tumors which requires new blood vessels to supply nutrients and excrete metabolites. Endothelial proliferation and new blood vessel formation promote an increase in solid tumors.

The key signal system regulates endothelial cell proliferation and migration is vascular endothelial growth factor (VEGF) and its receptor (VEGFR-1, -2 and -3). VEGFR-2 has a higher affinity and kinase activity, and plays a more important role in directly regulating angiogenesis, mitogenic signaling and permeability increasement. Vascular endothelial growth factor receptors (VEGFRs) are expressed at high levels in many human solid tumors, including glioma, lung cancer, breast cancer, renal cancer, ovarian cancer and gastrointestinal cancer.

VEGF/VEGFR-2 signaling pathway plays a critical role in tumor angiogenesis, and can inhibit angiogenesis by blocking or interfering with VEGF/VEGFR-2 signaling pathway in order to achieve the effect of controlling the growth of tumors. Thus, many small molecule VEGFR-2 inhibitors are being developed, some of which are useful in treating angiogenesis disorder related disease such as inflammatory diseases, retinopathy and so on. The present inventors have designed and synthesized naphthalene amides having novel structures and found small molecule VEGFR-2 inhibitors having good activity in the enzyme level and cellular level by optimizing the substituents.

SUMMARY OF THE INVENTION

In the present inventipon, a series of novel compounds were designed and synthesized by studing the crystal structure of VEGFR-2 and structure-activity relationship of other tyrosine kinase inhibitor, and screened by molecular and cellular screening model. These compounds can significantly inhibit the enzymic activity of VEGFR-2 at molecular level and significantly inhibit VEGF-induced human umbilical vein endothelial cells (HUVEC) proliferation at cellular level.

One object of the present invention is to provide naphthylamide compounds as represented by formula (I), medicinal salts, prodrugs and hydrates or solvates thereof:

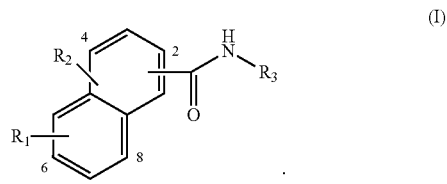

(I)

Another object of the present invention is to provide a method for preparing the above naphthylamide compounds.

A further object of the present invention is to provide a pharmaceutical composition containing a therapeutically effective amount of one or more of above naphthylamide compounds, medicinal salts, prodrugs and hydrates or solvates thereof.

A further object of the present invention is to provide a use of one or more of above naphthylamide compounds, medicinal salts, prodrugs and hydrates or solvates thereof as protein tyrosine kinase inhibitor, especially as a VEGFR-2 inhibitor, in the preparation of drugs for preventing and/or treating diseases associated with aberrant angiogenesis.

More specifically, the present invention relates to naphthylamide compounds of general formula (I), medicinal salts, prodrugs and hydrates or solvates thereof:

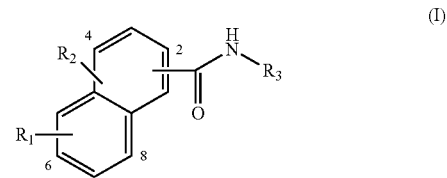

(I)

wherein, $R_1$ may be located at any one of 5-8 positions on the naphthalene ring, and is a substituted or unsubstituted 5-16 membered monocyclic, dicyclic or tricyclic heteroaryl containing 1-5 hetero atoms selected from the group comprising N, O, S and P, preferably is a substituted or unsubstituted 5-10 membered monocyclic or dicyclic heteroaryl containing 1-3 hetero atoms selected from the group comprising N, O and S, more preferably a substituted or unsubstituted group as follows: pyrnzolyl, furyl, pyrrolyl, pyridyl, indazolyl (e.g., 1H-indazolyl, 2H-indazolyl), furo[3,2-c]pyridyl, thieno[3,2-c]pyridyl, thieno[2,3-d]pyrimidinyl, benzo[d]isoxazolyl, benzo[d]isothiazolyl, indolyl, quinolyl or isoquinolyl; most preferably a substituted or unsubstituted group as follows: indazolyl (eg, 1H-indazolyl), furo[3,2-c]pyridyl, thieno[3,2-c]pyridyl or thieno[2,3-d]pyrimidinyl, benzo[d]isoxazolyl; in the case of substitution, the substituent may be 1 to 3 substituents, said substituent is independently selected from the group comprising amino, C1-C3 alkyl, C1-C3 alkoxy, halogen, pyrazolyl, C1-C3 alkyl-substituted pyrazolyl, C1-C3 hydroxyalkyl-substituted pyrazolyl, preferably amino, methyl, methoxy, F, Cl, Br, pyrazolyl, methyl-substituted pyrazolyl and hydroxyethyl-substituted pyrazolyl;

in most preferred embodiment, $R_1$ is the following structure:

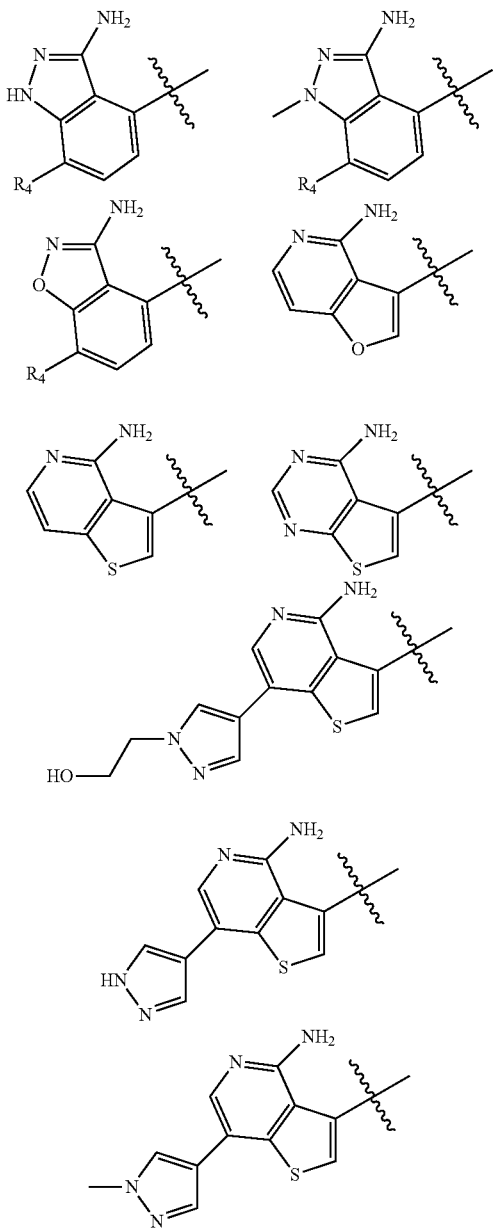

wherein, $R_4$ is selected from the group comprising hydrogen, halogen, C1-C3 alkyl and C1-C3 alkoxy, preferably selected from the group comprising hydrogen, F, Cl, Br, methyl and methoxy;

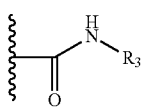

may be located at any one of 1-4 positions on the naphthalene ring;

$R_3$ is selected from the group consisting of hydrogen, C1-C6 alkyl, C3-C6 cycloalkyl, a substituted or unsubstituted phenyl and a substituted or unsubstituted 5-10 membered heteroaryl containing 1-5 hetero atoms selected from N, O and S, preferably selected from the group consisting of hydrogen, C1-C3 alkyl, C3-C6 cycloalkyl, a substituted or unsubstituted phenyl and a substituted or unsubstituted 5-6 membered heteroaryl containing 1-3 hetero atoms selected from N, O and S; more preferably selected from the group consisting of hydrogen, C1-C3 alkyl, C3-C6 cycloalkyl and a substituted or unsubstituted following group: phenyl, pyridyl, pyrimidinyl, oxazolyl, isoxazolyl, thienyl, imidazolyl, pyrazolyl, thiazolyl, furyl and pyrrolyl; most preferably selected from the group consisting of hydrogen, C1-C3 alkyl, C3-C6 cycloalkyl and a substituted or unsubstituted following group: phenyl, pyridyl, oxazolyl and isoxazolyl; in the case of substitution, the substituent may be 1 to 3 substituents and each substituent is independently selected from the group consisting of C1-C3 alkyl, C1-C3 alkoxy, C1-C3 haloalkyl, C1-C3 haloalkoxy, hydroxy, amino, nitro, and halogen; preferably selected from the group consisting of C1-C3 alkyl, methoxy, trifluoromethyl, trifluoromethoxy, hydroxy, amino, nitro, F, Cl and Br;

$R_2$ can be located at any one of positions 1-8 on the naphthalene ring except $R_1$ and

and is hydrogen or halogen; preferably hydrogen, F, Cl or Br.

Preferably, the naphthylamide compounds represented by general formula (I) are compounds represented by following formula (II):

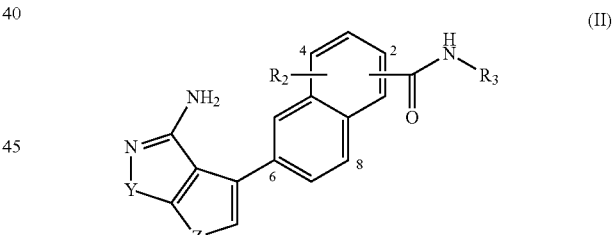

wherein, $R_2$ and

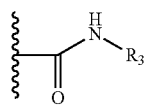

are defined as described in general formula (I);

Z is $C(R_5)$=CH, S or O;

Y is NH, NMe, O, CH=$C(R_6)$ or CH=N;

$R_5$ is selected from the group consisting of hydrogen, halogen, C1-C3 alkyl and C1-C3 alkoxy, preferably from the group consisting of hydrogen, F, Cl, Br, methyl and methoxy; $R_6$ is selected from the group consisting of hydrogen, pyrazolyl, C1-C3 alkyl-substituted pyrazolyl and C1-C3 hydroxyalkyl-substituted pyrazolyl, preferably from the group consisting of hydrogen, pyrazolyl, methyl-substituted pyrazolyl and hydroxyethyl-substituted pyrazolyl.

Preferably, naphthylamide compounds represented by general formula (I) are selected from the compounds represented by the following general formula:

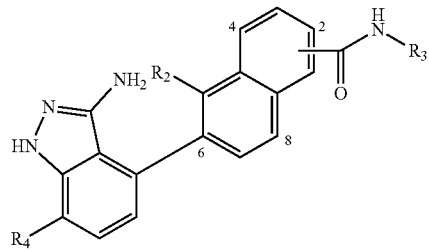
(III)

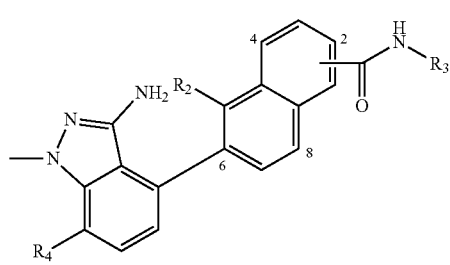
(IV)

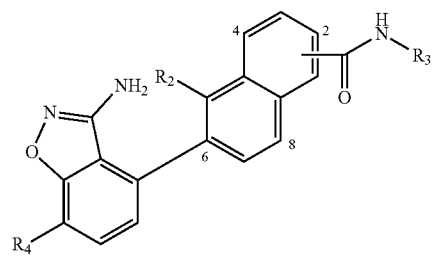
(V)

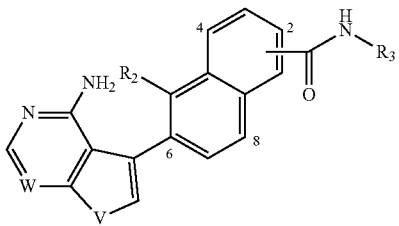
(VI)

wherein,

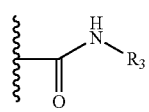

can be located at position 1 or 2 on the naphthalene ring; $R_2$ and $R_3$ are defined as described in general formula (I); $R_4$ is selected from the group consisting of hydrogen, halogen, C1-C3 alkyl and C1-C3 alkoxy, preferably from the group consisting of hydrogen, F, Cl, Br, methyl and methoxy;

V is S or O;

W is N or C($R_7$);

$R_7$ is selected from the group consisting of hydrogen, pyrazolyl, C1-C3 alkyl-substituted pyrazolyl and C1-C3 hydroxyalkyl-substituted pyrazolyl, preferably from the group consisting of hydrogen, pyrazolyl, methyl-substituted pyrazolyl and hydroxyethyl-substituted pyrazolyl.

Preferably, naphthylamide compound represented by general formula (I) in the present invention is selected from the compounds shown in Table 1:

TABLE 1

| compound | name | structural formula |
|---|---|---|
| I-1 | 6-(3-amino-1H-indazol-4-yl)-N-phenyl-1-naphthalenecarboxamide | |
| I-2 | 6-(4-aminofuro[3,2-c]pyridin-3-yl)-N-phenyl-1-naphthalenecarboxamide | |

TABLE 1-continued

| compound | name | structural formula |
|---|---|---|
| I-3 | 6-(4-aminothieno[3,2-c]pyridin-3-yl)-N-phenyl-1-naphthalenecarboxamide | |
| I-4 | 6-(4-aminothieno[2,3-d]pyrimidin-5-yl)-N-phenyl-1-naphthalenecarboxamide | |
| I-5 | 6-(4-amino-7-(1-(2-hydroxyethyl)-1H-pyrazol-4-yl)thieno[3,2-c]pyridin-3-yl)-N-phenyl-1-naphthalenecarboxamide | |
| I-6 | 6-(3-amino-1H-indazol-4-yl)-N-(o-methylphenyl)-1-naphthalenecarboxamide | |
| I-7 | 6-(3-amino-1H-indazol-4-yl)-N-(m-methylphenyl)-1-naphthalenecarboxamide | |
| I-8 | 6-(3-amino-1H-indazol-4-yl)-N-(p-methylphenyl)-1-naphthalenecarboxamide | |

TABLE 1-continued

| compound | name | structural formula |
|---|---|---|
| I-9 | 6-(3-amino-1H-indazol-4-yl)-N-(3-ethylphenyl)-1-naphthalenecarboxamide | |
| I-10 | 6-(3-amino-1H-indazol-4-yl)-N-(2-fluorophenyl)-1-naphthalenecarboxamide | |
| I-11 | 6-(3-amino-1H-indazol-4-yl)-N-(3-fluorophenyl)-1-naphthalenecarboxamide | |
| I-12 | 6-(3-amino-1H-indazol-4-yl)-N-(4-fluorophenyl)-1-naphthalenecarboxamide | |
| I-13 | 6-(3-amino-1H-indazol-4-yl)-N-(2,4-difluorophenyl)-1-naphthalenecarboxamide | |
| I-14 | 6-(3-amino-1H-indazol-4-yl)-N-(3,5-difluorophenyl)-1-naphthalenecarboxamide | |

TABLE 1-continued

| compound | name | structural formula |
|---|---|---|
| I-15 | 6-(3-amino-1H-indazol-4-yl)-N-(3-chlorophenyl)-1-naphthalene-carboxamide | |
| I-16 | 6-(3-amino-1H-indazol-4-yl)-N-(3-bromophenyl)-1-naphthalene-carboxamide | |
| I-17 | 6-(3-amino-1H-indazol-4-yl)-N-(3,5-dichlorophenyl)-1-naphtha-lenecarboxamide | |
| I-18 | 6-(3-amino-1H-indazol-4-yl)-N-(3,5-dibromophenyl)-1-naphtha-lenecarboxamide | |
| I-19 | 6-(3-amino-1H-indazol-4-yl)-N-(3-(trifluoromethyl)phenyl)-1-naphthalenecarboxamide | |
| I-20 | 6-(3-amino-1H-indazol-4-yl)-N-(2-fluoro-5-methylphenyl)-1-naphthalenecarboxamide | |

TABLE 1-continued

| compound | name | structural formula |
|---|---|---|
| I-21 | 6-(3-amino-1H-indazol-4-yl)-N-(4-fluoro-3-methylphenyl)-1-naphthalenecarboxamide | 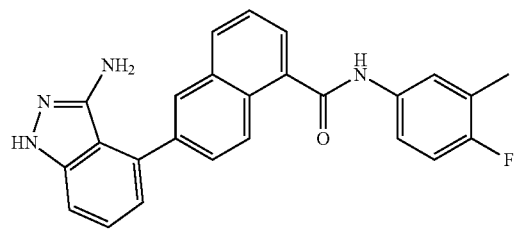 |
| I-22 | 6-(3-amino-1H-indazol-4-yl)-N-(2-fluoro-4-methylphenyl)-1-naphthalenecarboxamide | 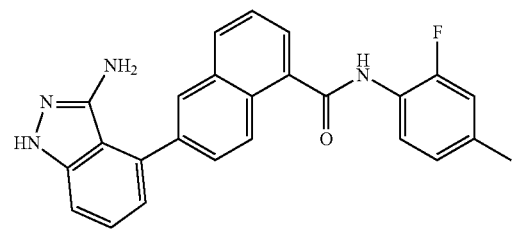 [SMILES: Cc1ccc(NC(=O)c2cccc3cc(-c4cccc5[nH]nc(N)c45)ccc23)cc1] |
| I-23 | 6-(3-amino-1H-indazol-4-yl)-N-(3-fluoro-4-methylphenyl)-1-naphthalenecarboxamide | 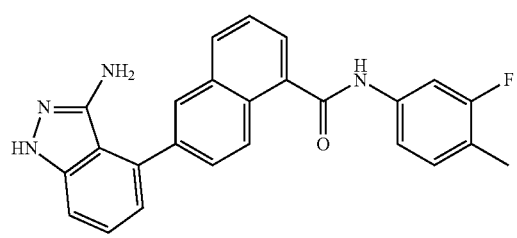 [SMILES: Cc1ccc(NC(=O)c2cccc3cc(-c4cccc5[nH]nc(N)c45)ccc23)cc1F] |
| I-24 | 6-(3-amino-1H-indazol-4-yl)-N-(5-methylisoxazol-3-yl)-1-naphthalenecarboxamide | 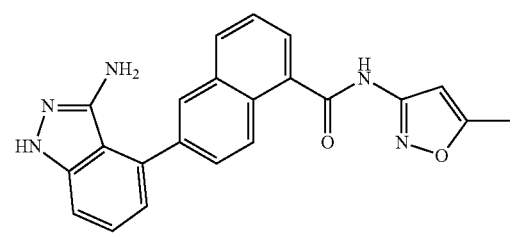 [SMILES: Cc1cc(NC(=O)c2cccc3cc(-c4cccc5[nH]nc(N)c45)ccc23)no1] |
| I-25 | 6-(3-amino-1H-indazol-4-yl)-N-(pyridin-3-yl)-1-naphthalenecarboxamide | 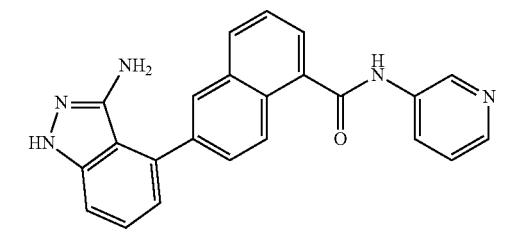 [SMILES: Nc1n[nH]c2cccc(-c3ccc4c(C(=O)Nc5cccnc5)cccc4c3)c12] |
| I-26 | 6-(3-amino-1H-indazol-4-yl)-N-ethyl-1-naphthalenecarboxamide | 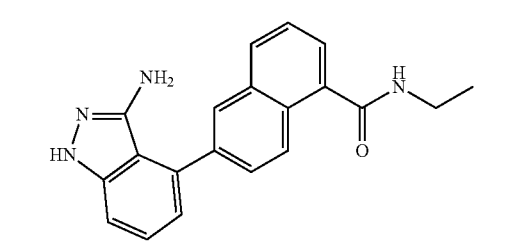 [SMILES: CCNC(=O)c1cccc2cc(-c3cccc4[nH]nc(N)c34)ccc12] |

TABLE 1-continued

| compound | name | structural formula |
|---|---|---|
| I-27 | 6-(3-amino-1H-indazol-4-yl)-N-cyclopropyl-1-naphthalenecarboxamide | 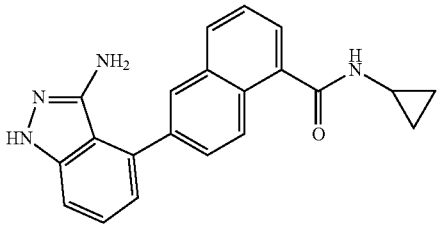 [SMILES: Nc1n[nH]c2cccc(-c3ccc4c(C(=O)NC5CC5)cccc4c3)c12] |
| I-28 | 6-(3-amino-1H-indazol-4-yl)-5-fluoro-N-phenyl-1-naphthalenecarboxamide | 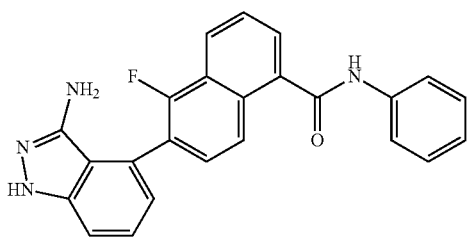 [SMILES: Nc1n[nH]c2cccc(-c3ccc4c(C(=O)Nc5ccccc5)cccc4c3F)c12] |
| I-29 | 6-(3-amino-1-methyl-1H-indazol-4-yl)-N-phenyl-1-naphthalenecarboxamide | 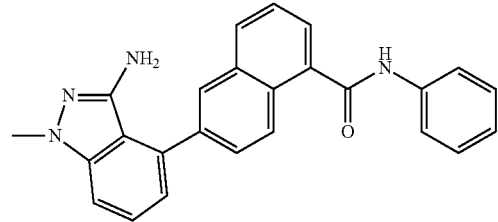 [SMILES: Cn1nc(N)c2c(-c3ccc4c(C(=O)Nc5ccccc5)cccc4c3)cccc21] |
| I-30 | 6-(3-amino-1H-indazol-4-yl)-N-phenyl-2-naphthalenecarboxamide | 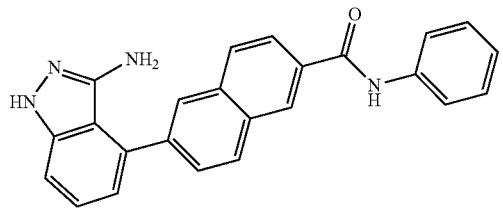 [SMILES: Nc1n[nH]c2cccc(-c3ccc4cc(C(=O)Nc5ccccc5)ccc4c3)c12] |
| I-31 | 6-(3-amino-1H-indazol-4-yl)-5-fluoro-N-phenyl-2-naphthalenecarboxamide | 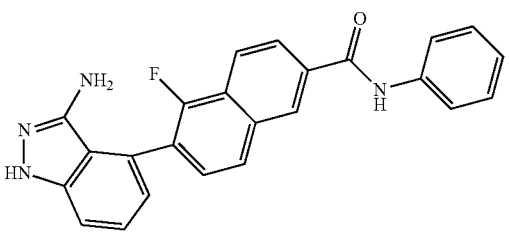 [SMILES: Nc1n[nH]c2cccc(-c3ccc4cc(C(=O)Nc5ccccc5)ccc4c3F)c12] |
| I-32 | 6-(3-amino-1H-indazol-4-yl)-5-chloro-N-phenyl-1-naphthalenecarboxamide | 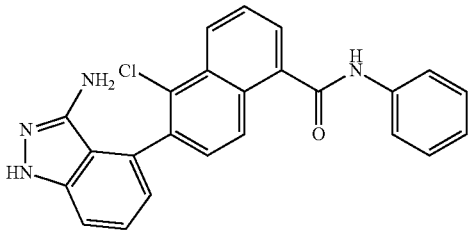 [SMILES: Nc1n[nH]c2cccc(-c3ccc4c(C(=O)Nc5ccccc5)cccc4c3Cl)c12] |

TABLE 1-continued

| compound | name | structural formula |
|---|---|---|
| I-33 | 6-(3-amino-7-fluoro-1H-indazol-4-yl)-N-phenyl-1-naphthalene-carboxamide | |
| I-34 | 6-(3-amino-7-bromo-1H-indazol-4-yl)-N-phenyl-1-naphthalene-carboxamide | |
| I-35 | 6-(3-amino-7-methyl-1H-indazol-4-yl)-N-phenyl-1-naphthalene-carboxamide | |
| I-36 | 6-(3-amino-1H-indazol-4-yl)-N-(3-methoxyphenyl)-1-naphthalene-carboxamide | |
| I-37 | 6-(3-amino-1H-indazol-4-yl)-N-(3-(trifluoromethoxy)phenyl)-1-naphthalenecarboxamide | |
| I-38 | 6-(3-amino-1H-indazol-4-yl)-N-(3-hydroxyphenyl)-1-naphthalene carboxamide | |

TABLE 1-continued

| compound | name | structural formula |
|---|---|---|
| I-39 | 6-(3-amino-1H-indazol-4-yl)-N-(3-nitrophenyl)-1-naphthalenecarboxamide | |
| I-40 | 6-(3-amino-1H-indazol-4-yl)-N-(3-aminophenyl)-1-naphthalenecarboxamide | |
| I-41 | 6-(3-aminobenzo[d]isoxazol-4-yl)-N-phenyl-1-naphthalenecarboxamide | |
| I-42 | 6-(3-amino-7-fluorobenzo[d]isoxazol-4-yl)-N-phenyl-1-naphthalenecarboxamide | |
| I-43 | 6-(3-amino-7-methylbenzo[d]isoxazol-4-yl)-N-phenyl-1-naphthalenecarboxamide | |
| I-44 | 6-(3-amino-7-methoxybenzo[d]isoxazol-4-yl)-N-phenyl-1-naphthalenecarboxamide | |

The pharmaceutically acceptable salts of the compounds of the present invention may be prepared through direct salt forming reaction of free base of compound and inorganic or organic acid. Inorganic or organic acid may be selected from the group consisting of hydrochloric acid, sulfuric acid, phosphoric acid, nitric acid, hydrofluoric acid, hydrobromic acid, formic acid, acetic acid, picric acid, citric acid, maleic acid, methanesulfonic acid, trifluoromethanesulfonic acid, ethanesulfonic acid, p-toluenesulfonic acid, and the like.

The present invention also relates to a preparation method of naphthylamide compounds of general formula (I), for example, including the following steps:

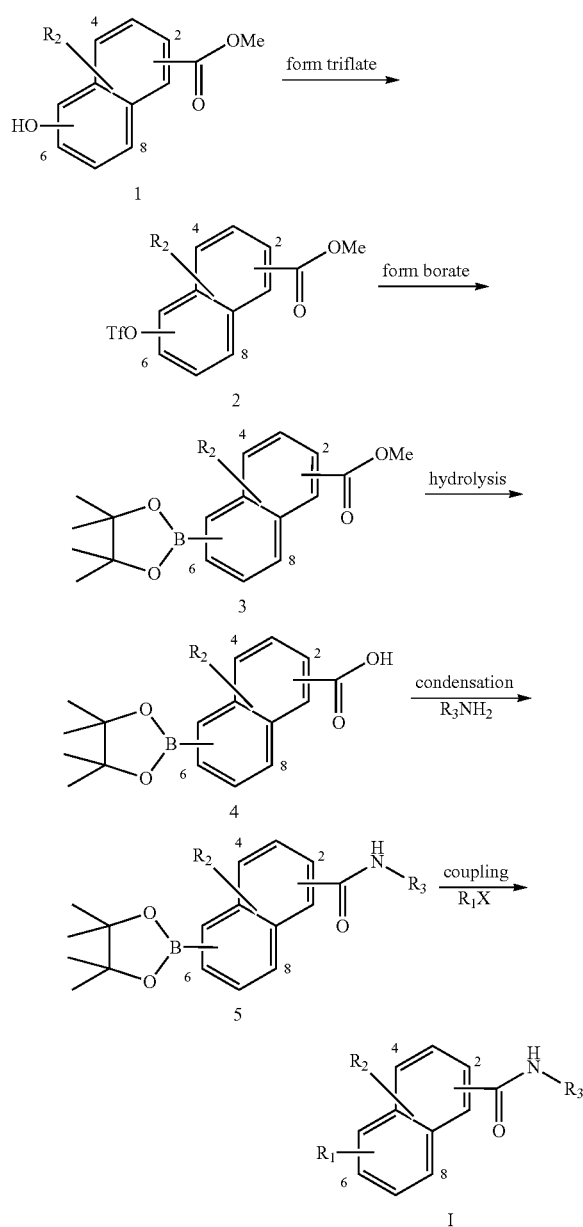

Starting from compound 1, hydroxyl was reacted to form triflate, and then to form borate. Naphthalate was hydrolyzed, then condensed with the corresponding ammonia/amine to obtain naphthylamide borate and finally coupled with a heteroaryl halide to give the target compound.

Specifically, the preparation method comprises the steps of:

1) Compound 1 is reacted with trifluoromethanesulfonic anhydride under basic condition to give compound 2;

2) Compound 2 and bis(pinacolato)diboron are subjected to coupling reaction in the presence of a palladium catalyst to obtain boronate 3;

3) Compound 3 was hydrolyzed with lithium hydroxide or sodium hydroxide to obtain compound 4;

4) Compound 4 and the corresponding ammonia/amine $R_3NH_2$ are subjected to condensation reaction under the effect of condensation agent such as dicyclohexyl carbodiimide (DCC), 1-(3-dimethylaminopropyl)-3-ethyl carbodiimide (EDC), 1-(3-dimethylaminopropyl)-3-ethyl carbodiimide hydrochloride (EDCI) or N,N'-diisopropyl carbodiimide (DIC) to obtain compound 5;

5) Compound 5 and the corresponding heteroaryl halide $R_1X$ are subjected to coupling reaction in the presence of a palladium catalyst to obtain the objective compound (I);

wherein, $R_1$, $R_2$ and $R_3$ are defined and preferred as above, X is halogen, preferably, Br or I.

The preparation method of naphthylamide compounds of the present invention has advantages such as mild reaction condition, abundant accessible raw materials, simple operation and post-processing and the like.

The present invention also relates to a pharmaceutical composition comprising a therapeutically effective amount of one or more of naphthylamide compounds of formula (I), pharmaceutically acceptable salts, prodrugs, hydrates and solvates thereof, and optionally a pharmaceutically acceptable carrier, which may be used in prevention and/or treatment of abnormal angiogenesis-related diseases. The pharmaceutical compositions may be prepared in various forms depending on different route of administration.

The present invention also relates to use of one or more of naphthylamide compounds of formula (I), pharmaceutically acceptable salts, prodrugs, hydrates and solvates thereof, or pharmaceutical composition comprising a therapeutically effective amount of one or more of naphthylamide compounds of formula (I), pharmaceutically acceptable salts, prodrugs, hydrates and solvates thereof in the preparation of drugs for the prevention and/or treatment of abnormal angiogenesis-related diseases, preferably as protein tyrosine kinase inhibitors, especially as VEGFR-2 inhibitors.

Wherein, the abnormal angiogenesis-related disease is selected from the group consisting of tumor, rheumatoid arthritis, age-related macular degeneration and psoriasis.

The tumor includes lung cancer, breast cancer, colon cancer, prostate cancer, pancreatic cancer, stomach cancer, liver cancer, ovarian cancer, renal cancer, glioma, melanoma, pancreatic cancer, head and neck cancer, bladder cancer, cervical cancer, cholangiocarcinoma, nasopharyngeal cancer, thyroid cancer, osteosarcoma, synovial sarcoma, rhabdomyosarcoma, fibrosarcoma, leiomyosarcoma, myeloma, lymphoma and the like.

DETAILED DESCRIPTION

The present invention will be further illustrated by the following examples. These examples are intended to illustrate the present invention, but not to limit the invention in any way. Unless otherwise defined or stated, all professional and scientific terms used herein have same meanings known as the skilled in the art.

EXAMPLE 1

6-(3-amino-1H-indazol-4-yl)-N-phenyl-1-naphthalenecarboxamide (I-1)

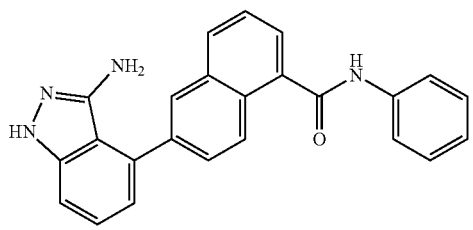 [SMILES: Nc1n[nH]c2cccc(-c3ccc4c(C(=O)Nc5ccccc5)cccc4c3)c12]

Step 1 methyl 6-(trifluoromethylsulfonyloxy)-1-naphthoate 5 g of 6-hydroxy-1-naphthoic acid was dissloved in 200 ml of methanol, and 2.8 ml of thionyl chloride was added dropwise with stirring. The mixture was heated under reflux for 2 hours, then cooled to room temperature and concentrated under reduced pressure to give methyl 6-hydroxy-1-naphthoate as tan solid which was directly used to the next step. 2.5 g of methyl 6-hydroxy-1-naphthoate was dissloved in 150 ml of dichloromethane and 6.5 ml of diisopropylethylamine and 3 ml of trifluoromethanesulfonic anhydride were added dropwise with stirring at −78° C. The mixture was stirred at −78° C. for another 1 hour and 100 ml of saturated aqueous ammonium chloride solution was poured in. The organic phase was separated, and the aqueous phase was extracted with dichloromethane. The combined organic phases was washed with saturated sodium chloride, dried over anhydrous sodium sulfate, filtered and concentrated. The residue was purified by column chromatography (ethyl acetate:petroleum ether=5:95) to give 3.5 g methyl 6-(trifluoromethylsulfonyloxy)-1-naphthoate as tan solid. Yield: 93%.

$^1$H NMR (300 MHz, DMSO-d$_6$) δ (ppm): 3.97 (s, 3H), 7.74-7.81 (m, 2H), 8.27 (dd, J=7.2, 1.2 Hz, 1H), 8.30 (d, J=3.0 Hz, 1H), 8.36 (d, J=8.1 Hz, 1H), 8.94 (d, J=9.3 Hz, 1H).

Step 2 methyl 6-(4,4,5,5-tetramethyl-1,3,2-dioxaborolan-2-yl)-1-naphthoate 3 g of methyl 6-(trifluoromethylsulfonyloxy)-1-naphthoate, 2.74 g of bis(pinacolato) diboron, 675 mg of [1,1'-Bis(diphenylphosphino)ferrocene]dichloropalladium(II), 498 mg of 1,1'-bis(diphenyphosphino)ferrocene, 2.87 g of potassium acetate and 60 ml of dioxane were added to the reaction flask, heated to 80° C. under Ar, stirred for 4 h and then cooled to room temperature. Water and ethyl acetate were added to separate. The aqueous phase was extracted with ethyl acetate. The combined organic phases was washed with saturated sodium chloride, dried over anhydrous sodium sulfate, filtered and concentrated. The residue was purified by column chromatography (ethyl acetate: petroleum ether=5:95) to give 2.74 g of methyl 6-(4,4,5,5-tetramethyl-1,3,2-dioxaborolan-2-yl)-1-naphthoate as brown oil. Yield: 98%.

$^1$H NMR (300 MHz, CDCl$_3$) δ (ppm): 1.40 (s, 12H), 4.01 (s, 3H), 7.50 (t, J=7.5 Hz, 1H), 7.97 (dd, J=8.7, 1.2 Hz, 1H), 8.06 (d, J=8.4 Hz, 1H), 8.22 (dd, J=7.5, 1.2 Hz, 1H), 8.40 (s, 1H), 8.88 (d, J=9.0 Hz, 1H).

Step 3

6-(4,4,5,5-tetramethyl-1,3,2-dioxaborolan-2-yl)-1-naphthoic acid 2.74 g of methyl 6-(4,4,5,5-tetramethyl-1,3,2-dioxaborolan-2-yl)-1-naphthoate was dissloved in 27 ml of tetrahydrofuran and 27 ml of water and 1.11 g of lithium hydrate was added with stirring. The mixture was stirred at room temperature for 12 h, then acidified with 2 mol/L hydrochloric acid and extracted with ethyl acetate. The combined organic phases was washed with saturated sodium chloride, dried over anhydrous sodium sulfate, filtered and concentrated. The residue was purified by column chromatography (methanol: dichloromethane=3:97) to give 2.04 g of 6-(4,4,5,5-tetramethyl-1,3,2-dioxaborolan-2-yl)-1-naphthoic acid as faint yellow solid. Yield: 78%.

$^1$H NMR (300 MHz, CDCl$_3$) δ (ppm): 1.41 (s, 12H), 7.55 (t, J=8.1 Hz, 1H), 7.80 (dd, J=8.4, 1.2 Hz, 1H), 8.13 (d, J=8.1 Hz, 1H), 8.43-8.46 (m, 2H), 9.05 (d, J=8.7 Hz, 1H).

Step 4

N-phenyl-6-(4,4,5,5-tetramethyl-1,3,2-dioxaborolan-2-yl)-1-naphthalene-carboxamide 80 mg of 6-(4,4,5,5-tetramethyl-1,3,2-dioxaborolan-2-yl)-1-naphthoic acid was dissloved in 8 ml of dichloromethane and 39 mg of 4-dimethylaminopyridine, 77 mg of 1-(3-dimethylaminopropyl)-3-ethylcarbodiimide hydrochloride were successively added with stirring at 0° C. After 15 minutes, 27 microliters aniline was added and then the mixture was warmed to room temperature and stirred overnight. On the next day the mixture was concentrated. The residue was purified by column chromatography (dichloromethane) to give 52 mg of N-phenyl-6-(4,4,5,5-tetramethyl-1,3,2-dioxaborolan-2-yl)-1-naphthalenecarboxamide as off-white solid. Yield: 52%.

$^1$H NMR (400 MHz, CDCl$_3$) δ (ppm): 1.40 (s, 12H), 7.19 (m, 2H), 7.41 (m, 2H), 7.52 (m, 1H), 7.69-7.01 (m, 3H), 7.79 (d, J=6.8 Hz, 1H), 7.92 (dd, J=8.4, 1.2 Hz, 1H), 8.02 (d, J=8.0 Hz, 1H), 8.34 (d, J=8.4 Hz, 1H), 8.15 (s, 1H).

Step 5

4-iodo-1H-indazol-3-amine 500 mg of 2-fluoro-6-iodobenzonitrile and 1.3 ml of hydrazine hydrate (85%) were dissloved in 10 ml of n-butanol and heated to 110° C. The mixture was stirred for 6 hours and then cooled to room temperature. Water and ethyl acetate were added to separate. The aqueous phase was extracted with ethyl acetate. The combined organic phases was washed with saturated sodium chloride, dried over anhydrous sodium sulfate, filtered and concentrated to dryness to give 502 mg of 4-iodo-1H-indazol-3-amine as tan solid. Yield: 96%.

$^1$H NMR (300 MHz, DMSO-d$_6$) δ (ppm): 5.05 (s, 2H), 6.90-6.96 (m, 1H), 7.29 (d, J=8.1 Hz, 1H), 7.34 (d, J=7.5 Hz, 1H), 11.80 (s, 1H).

Step 6

6-(3-amino-1H-indazol-4-yl)-N-phenyl-1-naphthalenecarboxamide (I-1)

30 mg of N-phenyl-6-(4,4,5,5-tetramethyl-1,3,2-dioxaborolan-2-yl)-1-naphthalene carboxamide, 17 mg of 4-iodo-1H-indazol-3-amine, 5 mg of palladium(II) bis(triphenyl phosphine) dichloride, 18 mg of sodium carbonate, 2 ml of ethanol, 1 ml of toluene and 1 ml of water were added to a reaction flask and heated under an argon atmosphere to 85° C. The mixture was stirred for 2 h and then cooled to room temperature. Water and ethyl acetate were added to separate. The aqueous phase was extracted with ethyl acetate. The combined organic phases was washed with saturated sodium chloride, dried over anhydrous sodium sulfate, filtered and concentrated. The residue was purified by column chromatography (methanol:dichloromethane=3:97) to give 14 mg of I-1 as off-white solid. Yield: 56%.

$^1$H NMR (400 MHz, DMSO-d$_6$) δ (ppm): 4.32 (s, 2H), 6.95 (t, J=3.6 Hz, 1H), 7.14 (t, J=8.0 Hz, 1H), 7.34-7.37 (m, 2H), 7.39 (t, J=8.0 Hz, 2H), 7.68 (dd, J=8.4, 7.2 Hz, 1H), 7.75 (dd, J=8.8, 2.0 Hz, 1H), 7.81 (dd, J=7.2, 0.8 Hz, 1H), 7.84 (d, J=8.0, 2H), 8.14 (d, J=2.0 Hz, 1H), 8.18 (d, J=8.4 Hz, 1H), 8.30 (d, J=9.2 Hz, 1H), 10.64 (s, 1H), 11.84 (s, 1H).

EXAMPLE 2

6-(4-aminofuro[3,2-c]pyridin-3-yl)-N-phenyl-1-naphthalenecarboxamide (I-2)

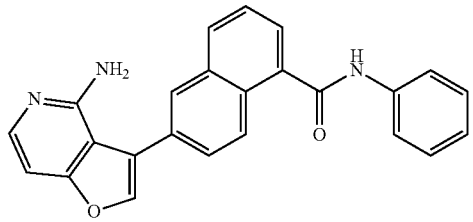 [SMILES: Nc1nccc2occ(-c3ccc4c(C(=O)Nc5ccccc5)cccc4c3)c12]

Step 1

3-bromofuro[3,2-c]pyridin-4-amine 200 mg of 3-bromo-4-chlorofuro[3,2-c]pyridine, 3 ml of concentrated aqueous ammonia and 3 ml of dioxane were added to a stainless steel sealed tube, closed and heated to 150° C. After stirred for 3 days, the mixture was cooled to room temperature. Water and ethyl acetate were added to separate. The aqueous phase was extracted with ethyl acetate. The combined organic phases was washed with saturated sodium chloride, dried over anhydrous sodium sulfate, filtered and concentrated to dryness to give 98 mg of 3-bromofuro[3,2-c]pyridin-4-amine as tan solid. Yield: 67%.

$^1$H NMR (300 MHz, DMSO-d$_6$) δ (ppm): 6.19 (s, 2H), 6.92 (d, J=6.0 Hz, 1H), 7.85 (d, J=6.0 Hz, 1H), 8.11 (s, 1H).

Step 2

6-(4-aminofuro[3,2-c]pyridin-3-yl)-N-phenyl-1-naphthalenecarboxamide (I-2)

4-iodo-1H-indazol-3-amine was replaced by 3-bromofuro[3,2-c]pyridin-4-amine and other raw materials, reagents and preparation method were identical with those in step 6 of example 1. I-2 as yellow solid was obtained.

$^1$H NMR (300 MHz, DMSO-d$_6$) δ (ppm): 5.68 (s, 2H), 7.02 (d, J=6.0 Hz, 1H), 7.11-7.16 (m, 1H), 7.36-7.42 (m, 2H), 7.66-7.71 (m, 1H), 7.76 (dd, J=9.0, 1.8 Hz, 1H), 7.82-7.85 (m, 3H), 7.92 (d, J=6.0 Hz, 1H), 8.13-8.19 (m, 3H), 8.34 (d, J=8.4 Hz, 1H), 10.62 (s, 1H).

EXAMPLE 3

6-(4-aminothieno[3,2-c]pyridin-3-yl)-N-phenyl-1-naphthalenecarboxamide (I-3)

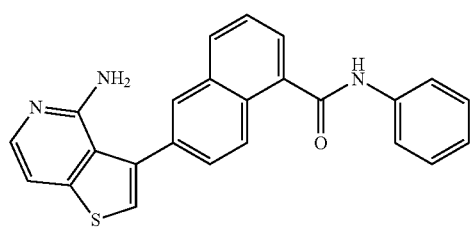 [SMILES: Nc1nccc2scc(-c3ccc4c(C(=O)Nc5ccccc5)cccc4c3)c12]

4-iodo-1H-indazol-3-amine was replaced by 3-bromothieno[3,2-c]pyridin-4-amine and other raw materials, reagents and preparation method were identical with those in step 6 of example 1. I-3 as yellow solid was obtained.

$^1$H NMR (300 MHz, DMSO-d$_6$) δ (ppm): 5.51 (s, 2H), 7.11-7.16 (m, 1H), 7.34-7.41 (m, 3H), 7.64 (s, 1H), 7.68-7.23 (m, 2H), 7.82-7.88 (m, 4H), 8.16-8.19 (m, 2H), 8.32 (d, J=9.0 Hz, 1H), 10.64 (s, 1H).

EXAMPLE 4

6-(4-aminothieno[2,3-d]pyrimidin-5-yl)-N-phenyl-1-naphthalenecarboxamide (I-4)

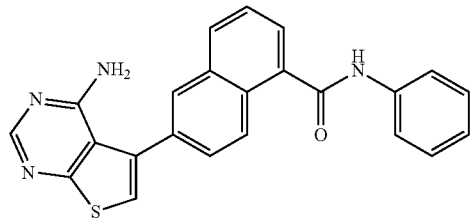 [SMILES: Nc1ncnc2scc(-c3ccc4c(C(=O)Nc5ccccc5)cccc4c3)c12]

Step 1

5-bromothieno[2,3-d]pyrimidin-4-amine 360 mg of 5-bromo-4-chlorothieno[2,3-d]pyrimidine and 20 ml of concentrated aqueous ammonia were added to a stainless steel sealed tube, closed and heated to 90° C. After stirred for 24 h, the mixture was cooled to room temperature, filtered and washed with water to give 272 mg of 5-bromothieno[2,3-d]pyrimidin-4-amine as yellow solid. Yield: 82%.

$^1$H NMR (300 MHz, DMSO-d$_6$) δ (ppm): 6.99-7.65 (br s, 1H), 7.78 (s, 1H), 8.32 (s, 1H).

Step 2

6-(4-aminothieno[2,3-d]pyrimidin-5-yl)-N-phenyl-1-naphthalenecarboxamide (I-4)

4-iodo-1H-indazol-3-amine was replaced by 5-bromothieno[2,3-d]pyrimidin-4-amine and other raw materials, reagents and preparation method were identical with those in step 6 of example 1 to give I-4 as white solid.

$^1$H NMR (300 MHz, DMSO-$d_6$) δ (ppm): 7.14 (t, J=7.2 Hz, 1H), 7.39-7.41 (m, 2H), 7.63 (s, 1H), 7.67-7.31 (m, 2H), 7.82-7.85 (m, 3H), 8.16-8.19 (m, 2H), 8.33 (d, J=9.0 Hz, 1H), 8.38 (s, 1H), 10.62 (s, 1H).

EXAMPLE 5

6-(4-amino-7-(1-(2-hydroxyethyl)-1H-pyrazol-4-yl) thieno[3,2-c]pyridin-3-yl)-N-phenyl-1-naphthalenecarboxamide (I-5)

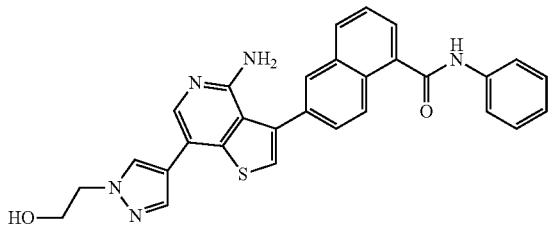 [SMILES: Nc1ncc(-c2cnn(CCO)c2)c2scc(-c3ccc4c(C(=O)Nc5ccccc5)cccc4c3)c12]

Step 1

2-(4-(4,4,5,5-tetramethyl-1,3,2-dioxaborolan-2-yl)-1H-pyrazol-1-)ethanol 100 mg of 4-(4,4,5,5-tetramethyl-1,3,2-dioxaborolan-2-yl)-1H-pyrazole and 91 mg of 1,3-dioxolan-2-one were dissloved in 2 ml of dimethylformamide. 336 mg of cesium carbonate was heated to 140° C., stirred for 0.5 h and then cooled to room temperature and concentrated. The residue was purified by column chromatography (ethyl acetate: petroleum ether=30:70) to give 93 mg of 2-(4-(4,4,5,5-tetramethyl-1,3,2-dioxaborolan-2-yl)-1H-pyrazol-1-yl)ethanol as pale yellow oil. Yield: 76%.

$^1$H NMR (300 MHz, DMSO-$d_6$) δ (ppm): 1.25 (s, 12H), 3.71 (q, J=5.4 Hz, 2H), 4.15 (t, J=5.4 Hz, 2H), 4.87 (t, J=5.4 Hz, 1H), 7.57 (s, 1H), 7.88 (s, 1H).

Step 2

6-(4-amino-7-iodothieno[3,2-c]pyridin-3-yl)-N-phenyl-1-naphthalenecarboxamide 80 mg of 6-(4-aminothieno[3,2-c]pyridin-3-yl)-N-phenyl-1-naphthalenecarboxamide (I-3) was dissloved in 3 ml of dimethylformamide. In an ice bath, 50 mg of N-iodosuccinimide was added with stirring and stirred overnight. On the next day the mixture was concentrated. The residue was purified by column chromatography (methanol:dichloromethane=2:98) to give 94 mg of 6-(4-amino-7-iodothieno[3,2-c]pyridin-3-yl)-N-phenyl-1-naphthalenecarboxamide as black solid. Yield: 90%.

$^1$H NMR (300 MHz, DMSO-$d_6$) δ (ppm): 5.58 (s, 2H), 7.13 (t, J=7.2 Hz, 1H), 7.39 (t, J=7.8 Hz, 2H), 7.68-7.73 (m, 3H), 7.82-7.85 (m, 3H), 8.06 (s, 1H), 8.16-8.19 (m, 2H), 8.32 (d, J=8.7 Hz, 1H), 10.64 (s, 1H).

Step 3

6-(4-amino-7-(1-(2-hydroxyethyl)-1H-pyrazol-4-yl) thieno[3,2-c]pyridin-3-yl)-N-phenyl-1-naphthalenecarboxamide (I-5)

26 mg of 6-(4-amino-7-iodothieno[3,2-c]pyridin-3-yl)-N-phenyl-1-naphthalene carboxamide, 24 mg of 2-(4-(4,4,5,5-tetramethyl-1,3,2-dioxaborolan-2-yl)-1H-pyrazol-1-yl) ethanol, 4 mg of palladium(II)bis(triphenylphosphine) dichloride, 13 mg of sodium carbonate, 2 ml of ethanol, 1 ml of toluene and 1 ml of water were added to a reaction flask and heated to 90° C. under Ar. After stirred for 4 h, the mixture was cooled to room temperature. Water and ethyl acetate were added to separate. The aqueous phase was extracted with ethyl acetate. The combined organic phases was washed with saturated sodium chloride, dried over anhydrous sodium sulfate, filtered and concentrated. The residue was purified by column chromatography (methanol: dichloromethane=5:95) to give 8 mg of I-5 as brown solid. Yield: 32%.

$^1$H NMR (400 MHz, DMSO-$d_6$) δ (ppm): 3.81 (q, J=5.2 Hz, 2H), 4.25 (t, J=5.6 Hz, 2H), 5.02 (t, J=5.2 Hz, 1H), 5.68 (s, 2H), 7.14 (t, J=7.2 Hz, 1H), 7.39 (t, J=8.0 Hz, 2H), 7.70-7.74 (m, 2H), 7.77 (s, 1H), 7.83-7.86 (m, 3H), 7.96 (s, 1H), 8.11 (s, 1H), 8.18-8.22 (m, 3H), 8.33 (d, J=8.8 Hz, 1H), 10.67 (s, 1H).

EXAMPLE 6

6-(3-amino-1H-indazol-4-yl)-N-(o-methylphenyl)-1-naphthalenecarboxamide (I-6)

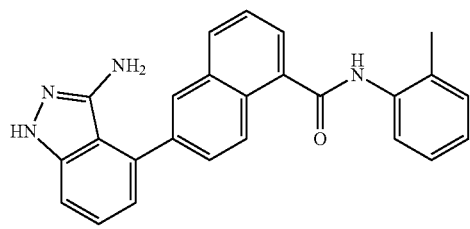 [SMILES: Cc1ccccc1NC(=O)c1cccc2cc(-c3cccc4[nH]nc(N)c34)ccc12]

Step 1

6-(4,4,5,5-tetramethyl-1,3,2-dioxaborolan-2-yl)-N-(o-methylphenyl)-1-naphthalenecarboxamide Phenylamine was replaced by o-methylphenylamine and other raw materials, reagents and preparation method were identical with those in step 4 of example 1 to give 6-(4,4,5,5-tetramethyl-1,3,2-dioxaborolan-2-yl)-N-(o-methylphenyl)-1-naphthalenecarboxamide as yellow solid.

$^1$H NMR (400 MHz, CDCl$_3$) δ (ppm): 1.40 (s, 12H), 2.32 (s, 3H), 7.14-7.17 (m, 1H), 7.25-7.26 (m, 1H), 7.31-7.35 (m, 1H), 7.51-7.55 (m, 2H), 7.83 (d, J=6.4 Hz, 1H), 7.94 (dd, J=8.4, 1.2 Hz, 1H), 8.03 (d, J=8.0 Hz, 1H), 8.14 (d, J=7.2 Hz, 1H), 8.40 (d, J=8.4 Hz, 1H), 8.42 (s, 1H).

Step 2

6-(3-amino-1H-indazol-4-yl)-N-(o-methylphenyl)-1-naphthalenecarboxamide (I-6)

N-phenyl-6-(4,4,5,5-tetramethyl-1,3,2-dioxaborolan-2-yl)-1-naphthalenecarboxamide was replaced by 6-(4,4,5,5-tetramethyl-1,3,2-dioxaborolan-2-yl)-N-(o-methylphenyl)-1-naphthalenecarboxamide and other raw materials, reagents and preparation method were identical with those in step 6 of example 1 to give I-6 as tan solid.

$^1$H NMR (400 MHz, DMSO-d$_6$) δ (ppm): 2.36 (s, 3H), 4.33 (s, 2H), 6.94-6.96 (m, 1H), 7.20-7.22 (m, 1H), 7.25-7.32 (m, 2H), 7.35-7.36 (m, 2H), 7.54 (d, J=7.6 Hz, 1H), 7.69 (t, J=7.6 Hz, 1H), 7.77 (dd, J=8.8, 2.0 Hz, 1H), 7.88 (d, J=7.2 Hz, 1H), 8.13 (d, J=1.6 Hz, 1H), 8.18 (d, J=8.0 Hz, 1H), 8.42 (d, J=8.8 Hz, 1H), 10.12 (s, 1H), 11.84 (s, 1H).

EXAMPLE 7

6-(3-amino-1H-indazol-4-yl)-N-(m-methylphenyl)-1-naphthalenecarboxamide (I-7)

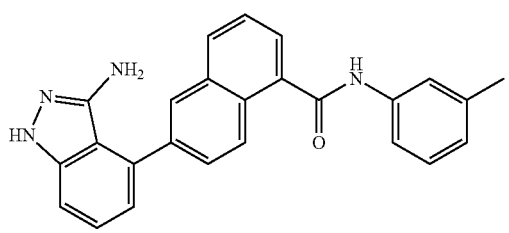 [SMILES: Cc1cccc(NC(=O)c2cccc3cc(-c4cccc5[nH]nc(N)c45)ccc23)c1]

Step 1

6-(4,4,5,5-tetramethyl-1,3,2-dioxaborolan-2-yl)-N-(m-methylphenyl)-1-naphthalenecarboxamide Phenylamine was replaced by m-methylphenylamine and other raw materials, reagents and preparation method were identical with those in step 4 of example 1 to give 6-(4,4,5,5-tetramethyl-1,3,2-dioxaborolan-2-yl)-N-(m-methylphenyl)-1-naphthalenecarboxamide as tan solid.

$^1$H NMR (300 MHz, CDCl$_3$) δ (ppm): 1.40 (s, 12H), 2.39 (s, 3H), 6.99 (d, J=7.5 Hz, 1H), 7.27 (t, J=8.1 Hz, 1H), 7.42-7.50 (m, 2H), 7.56 (s, 1H), 7.69-7.75 (m, 2H), 7.90 (dd, J=8.4, 0.9 Hz, 1H), 7.99 (d, J=8.4 Hz, 1H), 8.32 (d, J=9.0 Hz, 1H), 8.40 (s, 1H).

Step 2

6-(3-amino-1H-indazol-4-yl)-N-(m-methylphenyl)-1-naphthalenecarboxamide (I-7)

N-phenyl-6-(4,4,5,5-tetramethyl-1,3,2-dioxaborolan-2-yl)-1-naphthalenecarboxamide was replaced by 6-(4,4,5,5-tetramethyl-1,3,2-dioxaborolan-2-yl)-N-(m-methylphenyl)-1-naphthalenecarboxamide and other raw materials, reagents and preparation method were identical with those in step 6 of example 1 to give I-7 as off-white solid.

$^1$H NMR (400 MHz, DMSO-d$_6$) δ (ppm): 2.34 (s, 3H), 4.32 (s, 2H), 6.93-6.97 (m, 2H), 7.26 (m, 1H), 7.34-7.35 (m, 2H), 7.60 (d, J=8.0 Hz, 1H), 6.67 (t, J=7.6 Hz, 1H), 7.71 (s, 1H), 7.75 (dd, J=8.8, 1.6 Hz, 1H), 7.79 (d, J=6.8 Hz, 1H), 8.13 (d, J=1.2 Hz, 1H), 8.18 (d, J=8.0 Hz, 1H), 8.29 (d, J=8.8 Hz, 1H), 10.57 (s, 1H), 11.84 (s, 1H).

EXAMPLE 8

6-(3-amino-1H-indazol-4-yl)-N-(p-methylphenyl)-1-naphthalenecarboxamide (I-8)

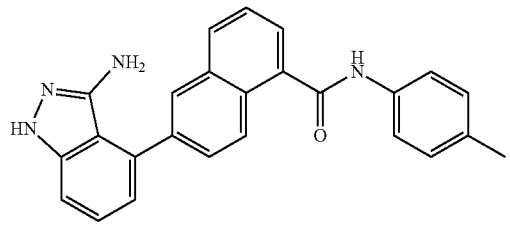 [SMILES: Cc1ccc(NC(=O)c2cccc3cc(-c4cccc5[nH]nc(N)c45)ccc23)cc1]

Step 1

6-(4,4,5,5-tetramethyl-1,3,2-dioxaborolan-2-yl)-N-(p-methylphenyl)-1-naphthalenecarboxamide Phenylamine was replaced by p-methylphenylamine and other raw materials, reagents and preparation method were identical with those in step 4 of example 1 to give 6-(4,4,5,5-tetramethyl-1,3,2-dioxaborolan-2-yl)-N-(p-methylphenyl)-1-naphthalenecarboxamide as yellow solid.

$^1$H NMR (400 MHz, CDCl$_3$) δ (ppm): 1.40 (s, 12H), 2.36 (s, 3H), 7.21 (d, J=8.0 Hz, 2H), 7.49-7.53 (m, 1H), 7.57 (d, J=8.4 Hz, 2H), 7.64 (s, 1H), 7.78 (d, J=7.2 Hz, 1H), 7.92 (dd, J=8.4, 0.8 Hz, 1H), 7.80 (d, J=8.4 Hz, 1H), 8.34 (d, J=8.4 Hz, 1H), 8.41 (s, 1H).

Step 2

6-(3-amino-1H-indazol-4-yl)-N-(p-methylphenyl)-1-naphthalenecarboxamide (I-8)

N-phenyl-6-(4,4,5,5-tetramethyl-1,3,2-dioxaborolan-2-yl)-1-naphthalenecarboxamide was replaced by 6-(4,4,5,5-tetramethyl-1,3,2-dioxaborolan-2-yl)-N-(p-methylphenyl)-1-naphthalenecarboxamide and other raw materials, reagents and preparation method were identical with those in step 6 of example 1 to give I-8 as tan solid.

$^1$H NMR (400 MHz, DMSO-d$_6$) δ (ppm): 2.30 (s, 3H), 4.32 (s, 2H), 6.94 (t, J=4.0 Hz, 1H), 7.19 (d, J=8.0 Hz, 2H), 7.34-7.35 (m, 2H), 7.65-7.80 (m, 5H), 8.13 (s, 1H), 8.18 (d, J=8.0 Hz, 1H), 8.30 (d, J=8.8 Hz, 1H), 10.56 (s, 1H), 11.85 (s, 1H).

EXAMPLE 9

6-(3-amino-1H-indazol-4-yl)-N-(3-ethylphenyl)-1-naphthalenecarboxamide (I-9)

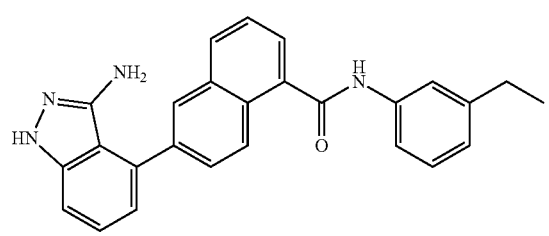 [SMILES: CCc1cccc(NC(=O)c2cccc3cc(-c4cccc5[nH]nc(N)c45)ccc23)c1]

Step 1

N-(3-ethylphenyl)-6-(4,4,5,5-tetramethyl-1,3,2-dioxaborolan-2-yl)-1-naphthalenecarboxamide Phenylamine was replaced by m-ethylphenylamine and other raw materials, reagents and preparation method were identical with those in step 4 of example 1 to give N-(3-ethylphenyl)-6-(4,4,5,5-tetramethyl-1,3,2-dioxaborolan-2-yl)-1-naphthalenecarboxamide as tan solid.

$^1$H NMR (400 MHz, CDCl$_3$) δ (ppm): 1.28 (t, J=7.6 Hz, 3H), 1.40 (s, 12H), 2.69 (q, J=7.6 Hz, 2H), 7.04 (d, f=7.6 Hz, 1H), 7.32 (t, J=8.0 Hz, 1H), 7.49-7.53 (m, 2H), 7.57 (s, 1H), 7.65 (s, 1H), 7.78 (d, J=6.8 Hz, 1H), 7.92 (dd, J=8.4, 1.2 Hz, 1H), 8.01 (d, J=8.4 Hz, 1H), 8.35 (d, J=8.4 Hz, 1H), 8.42 (s, 1H).

Step 2

6-(3-amino-1H-indazol-4-yl)-N-(3-ethylphenyl)-1-naphthalenecarboxamide (I-9)

N-phenyl-6-(4,4,5,5-tetramethyl-1,3,2-dioxaborolan-2-yl)-1-naphthalenecarboxamide was replaced by N-(3-ethylphenyl)-6-(4,4,5,5-tetramethyl-1,3,2-dioxaborolan-2-yl)-1-naphthalene carboxamide and other raw materials, reagents and preparation method were identical with those in step 6 of example 1 to give I-9 as white solid.

$^1$H NMR (400 MHz, DMSO-d$_6$) δ (ppm): 1.21 (t, J=7.6 Hz, 3H), 2.63 (q, J=7.6, 2H), 4.32 (s, 2H), 6.94 (t, J=4.0 Hz, 1H), 6.99 (d, J=7.6 Hz, 1H), 7.27-7.31 (m, 1H), 7.33-7.36 (m, 2H), 7.62-7.69 (m, 2H), 7.73-7.80 (m, 3H), 8.13 (d, J=1.2 Hz, 1H), 8.18 (d, J=8.0 Hz, 1H), 8.30 (d, J=8.4 Hz, 1H), 10.58 (s, 1H), 11.84 (s, 1H).

EXAMPLE 10

6-(3-amino-1H-indazol-4-yl)-N-(2-fluorophenyl)-1-naphthalenecarboxamide (I-10)

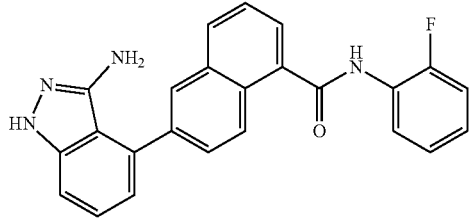 [SMILES: Nc1n[nH]c2cccc(-c3ccc4c(C(=O)Nc5ccccc5F)cccc4c3)c12]

Step 1

N-(2-fluorophenyl)-6-(4,4,5,5-tetramethyl-1,3,2-dioxaborolan-2-yl)-1-naphthalenecarboxamide Phenylamine was replaced by 2-fluorophenylamine and other raw materials, reagents and preparation method were identical with those in step 4 of example 1 to give N-(2-fluorophenyl)-6-(4,4, 5, 5-tetramethyl-1,3,2-dioxaborolan-2-yl)-1-naphthalenecarboxamide as yellow solid.

$^1$H NMR (400 MHz, CDCl$_3$) δ (ppm): 1.40 (s, 12H), 7.12-7.16 (m, 2H), 7.24-7.26 (m, 1H), 7.53 (dd, J=8.4, 7.2 Hz, 1H), 7.82 (dd, J=7.2, 0.8 Hz, 1H), 7.93-7.95 (m, 2H), 8.04 (d, J=8.0 Hz, 1H), 8.37 (d, J=8.8 Hz, 1H), 8.43 (s, 1H), 8.59 (s, 1H).

Step 2

6-(3-amino-1H-indazol-4-yl)-N-(2-fluorophenyl)-1-naphthalenecarboxamide (I-10)

N-phenyl-6-(4,4, 5,5-tetramethyl-1,3,2-dioxaborolan-2-yl)-1-naphthalenecarboxamide was replaced by N-(2-fluorophenyl)-6-(4,4, 5, 5-tetramethyl-1,3,2-dioxaborolan-2-yl)-1-naphthalenecarboxamide and other raw materials, reagents and preparation method were identical with those in step 6 of example 1 to give off-white solid I-10.

$^1$H NMR (400 MHz, DMSO-d$_6$) δ (ppm): 4.32 (s, 2H), 6.95 (t, J=4.0 Hz, 1H), 7.27-7.36 (m, 5H), 6.68 (t, J=7.6 Hz, 1H), 7.76 (dd, J=8.8, 2.0 Hz, 1H), 7.81-7.86 (m, 2H), 8.13 (d, J=1.6 Hz, 1H), 8.19 (d, J=8.4 Hz, 1H), 8.38 (d, J=8.8 Hz, 1H), 10.43 (s, 1H), 11.84 (s, 1H).

EXAMPLE 11

6-(3-amino-1H-indazol-4-yl)-N-(3-fluorophenyl)-1-naphthalenecarboxamide (I-11)

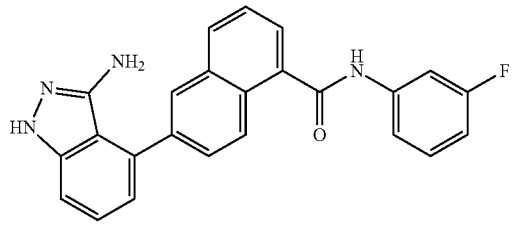 [SMILES: Nc1n[nH]c2cccc(-c3ccc4c(C(=O)Nc5cccc(F)c5)cccc4c3)c12]

Step 1

N-(3-fluorophenyl)-6-(4,4,5,5-tetramethyl-1,3,2-dioxaborolan-2-yl)-1-naphthalenecarboxamide Phenylamine was replaced by 3-fluorophenylamine and other raw materials, reagents and preparation method were identical with those in step 4 of example 1 to give N-(3-fluorophenyl)-6-(4,4,5,5-tetramethyl-1,3,2-dioxaborolan-2-yl)-1-naphthalenecarboxamide as faint yellow solid.

$^1$H NMR (400 MHz, CDCl$_3$) δ (ppm): 1.40 (s, 12H), 6.87-6.91 (m, 1H), 7.29-7.35 (m, 2H), 7.50-7.54 (m, 1H), 7.69-7.72 (m, 1H), 7.75-7.79 (m, 2H), 7.93 (d, J=8.8 Hz, 1H), 8.03 (d, J=8.0 Hz, 1H), 8.31 (d, J=8.8 Hz, 1H), 8.42 (s, 1H).

Step 2

6-(3-amino-1H-indazol-4-yl)-N-(3-fluorophenyl)-1-naphthalenecarboxamide (I-11)

N-phenyl-6-(4,4,5,5-tetramethyl-1,3,2-dioxaborolan-2-yl)-1-naphthalenecarboxamide was replaced by N-(3-fluorophenyl)-6-(4,4,5,5-tetramethyl-1,3,2-dioxaborolan-2-yl)-1-naphthalene carboxamide and other raw materials, reagents and preparation method were identical with those in step 6 of example 1 to give off-white solid I-11.

$^1$H NMR (400 MHz, DMSO-d$_6$) δ (ppm): 4.32 (s, 2H), 6.94-7.00 (m, 2H), 7.35-7.36 (m, 2H), 7.40-7.45 (m, 1H), 7.58 (d, J=8.4 Hz, 1H), 7.67-7.71 (m, 1H), 7.76 (dd, J=8.8, 2.0 Hz, 1H), 7.82-7.86 (m, 2H), 8.14 (d, J=1.6 Hz, 1H), 8.20 (d, J=8.4 Hz, 1H), 8.30 (d, J=8.8 Hz, 1H), 10.86 (s, 1H), 11.85 (s, 1H).

EXAMPLE 12

6-(3-amino-1H-indazol-4-yl)-N-(4-fluorophenyl)-1-naphthalenecarboxamide (I-12)

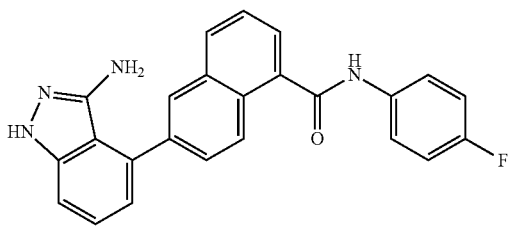 [SMILES: Nc1n[nH]c2cccc(-c3ccc4c(C(=O)Nc5ccc(F)cc5)cccc4c3)c12]

Step 1

N-(4-fluorophenyl)-6-(4,4,5,5-tetramethyl-1,3,2-dioxaborolan-2-yl)-1-naphthalenecarboxamide Phenylamine was replaced by 4-fluorophenylamine and other raw materials, reagents and preparation method were identical with those in step 4 of example 1 to give N-(4-fluorophenyl)-6-(4,4,5,5-tetramethyl-1,3,2-dioxaborolan-2-yl)-1-naphthalenecarboxamide as off-white solid.

$^1$H NMR (400 MHz, CDCl$_3$) δ (ppm): 1.40 (s, 12H), 7.10 (t, J=8.4 Hz, 2H), 7.50-7.54 (m, 1H), 7.64-7.69 (m, 3H), 7.78 (d, J=6.4 Hz, 1H), 7.93 (dd, J=8.4, 1.2 Hz, 1H), 8.02 (d, J=8.0 Hz, 1H), 8.32 (d, J=8.4 Hz, 1H), 8.42 (s, 1H).

Step 2

6-(3-amino-1H-indazol-4-yl)-N-(4-fluorophenyl)-1-naphthalenecarboxamide (I-12)

N-phenyl-6-(4,4, 5, 5-tetramethyl-1,3,2-dioxaborolan-2-yl)-1-naphthalenecarboxamide was replaced by N-(4-fluorophenyl)-6-(4,4,5,5-tetramethyl-1,3,2-dioxaborolan-2-yl)-1-naphthalene carboxamide and other raw materials, reagents and preparation method were identical with those in step 6 of example 1 to give off-white solid I-12.

$^1$H NMR (300 MHz, DMSO-d$_6$) δ (ppm): 4.31 (s, 2H), 6.93-6.96 (m, 1H), 7.24 (t, J=9.0 Hz, 2H), 7.34-7.36 (m, 2H), 7.65-7.70 (m, 1H), 7.75 (dd, J=8.7, 1.8 Hz, 1H), 7.80-7.88 (m, 3H), 8.13 (d, J=1.5 Hz, 1H), 8.18 (d, J=8.1 Hz, 1H), 8.31 (d, J=9.0 Hz, 1H), 10.68 (s, 1H), 11.83 (s, 1H).

EXAMPLE 13

6-(3-amino-1H-indazol-4-yl)-N-(2,4-difluorophenyl)-1-naphthalenecarboxamide (I-13)

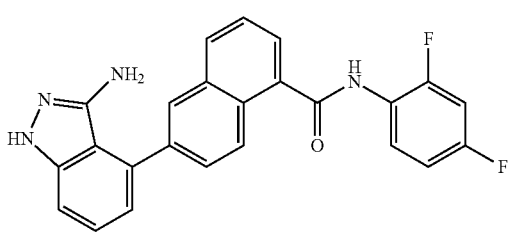 [SMILES: Nc1n[nH]c2cccc(-c3ccc4c(C(=O)Nc5ccc(F)cc5F)cccc4c3)c12]

Step 1

N-(2,4-difluorophenyl)-6-(4,4,5,5-tetramethyl-1,3,2-dioxaborolan-2-yl)-1-naphthalenecarboxamide Phenylamine was replaced by 2,4-difluorophenylamine and other raw materials, reagents and preparation method were identical with those in step 4 of example 1 to give N-(2,4-difluorophenyl)-6-(4,4,5,5-tetramethyl-1,3,2-dioxaborolan-2-yl)-1-naphthalenecarboxamide as yellow solid.

$^1$H NMR (400 MHz, CDCl$_3$) δ (ppm): 1.40 (s, 12H), 6.92-7.03 (m, 2H), 7.54-7.57 (m, 1H), 7.83-7.84 (m, 2H), 7.96 (dd, J=8.4, 1.2 Hz, 1H), 8.06 (d, J=8.0 Hz, 1H), 8.37 (d, J=8.8 Hz, 1H), 8.44 (s, 1H), 8.55-8.58 (m, 1H).

Step 2

6-(3-amino-1H-indazol-4-yl)-N-(2,4-difluorophenyl)-1-naphthalenecarboxamide (I-13)

N-phenyl-6-(4,4, 5,5-tetramethyl-1,3,2-dioxaborolan-2-yl)-1-naphthalenecarboxamide was replaced by N-(2,4-difluorophenyl)-6-(4,4,5,5-tetramethyl-1,3,2-dioxaborolan-2-yl)-1-naphthalenecarboxamide and other raw materials, reagents and preparation method were identical with those in step 6 of example 1 to give white solid I-13.

$^1$H NMR (400 MHz, DMSO-d$_6$) δ (ppm): 4.32 (s, 2H), 6.95 (t, J=4.0 Hz, 1H), 7.18-7.22 (m, 1H), 7.35-7.36 (m, 2H), 7.39-7.44 (m, 1H), 7.68 (t, J=7.6 Hz, 1H), 7.75-7.80 (m, 2H), 7.85 (d, J=6.8 Hz, 1H), 8.13 (d, J=1.6 Hz, 1H), 8.19 (d, J=8.0 Hz, 1H), 8.38 (d, J=8.8 Hz, 1H), 10.44 (s, 1H), 11.85 (s, 1H).

EXAMPLE 14

6-(3-amino-1H-indazol-4-yl)-N-(3,5-difluorophenyl)-1-naphthalenecarboxamide (I-14)

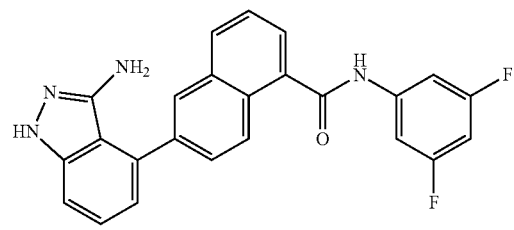 [SMILES: Nc1n[nH]c2cccc(-c3ccc4c(C(=O)Nc5cc(F)cc(F)c5)cccc4c3)c12]

Step 1

N-(3,5-difluorophenyl)-6-(4,4,5,5-tetramethyl-1,3,2-dioxaborolan-2-yl)-1-naphthalenecarboxamide Phenylamine was replaced by 3,5-difluorophenylamine and other raw materials, reagents and preparation method were identical with those in step 4 of example 1 to give N-(3,5-difluorophenyl)-6-(4,4,5,5-tetramethyl-1,3,2-dioxaborolan-2-yl)-1-naphthalenecarboxamide as off-white solid.

$^1$H NMR (400 MHz, CDCl$_3$) δ (ppm): 1.40 (s, 12H), 6.61-6.66 (m, 1H), 7.31 (d, J=7.2 Hz, 2H), 7.49-7.53 (m, 1H), 7.75-7.77 (m, 2H), 7.94 (d, J=8.8 Hz, 1H), 8.03 (d, J=8.4 Hz, 1H), 8.28 (d, J=8.4 Hz, 1H), 8.42 (s, 1H).

Step 2

6-(3-amino-1H-indazol-4-yl)-N-(3,5-difluorophenyl)-1-naphthalenecarboxamide (I-14)

N-phenyl-6-(4,4,5,5-tetramethyl-1,3,2-dioxaborolan-2-yl)-1-naphthalenecarboxamide was replaced by N-(3,5-difluorophenyl)-6-(4,4,5,5-tetramethyl-1,3,2-dioxaborolan-2-yl)-1-naphthalenecarboxamide and other raw materials, reagents and preparation method were identical with those in step 6 of example 1 to give faint yellow solid I-14.
$^1$H NMR (400 MHz, DMSO-$d_6$) δ (ppm): 4.32 (s, 2H), 6.95-7.02 (m, 2H), 7.35 (s, 2H), 7.57-7.59 (s, 2H), 7.69-7.85 (m, 3H), 8.15-8.31 (m, 3H), 11.02 (s, 1H), 11.85 (s, 1H).

EXAMPLE 15

6-(3-amino-1H-indazol-4-yl)-N-(3-chlorophenyl)-1-naphthalenecarboxamide (I-15)

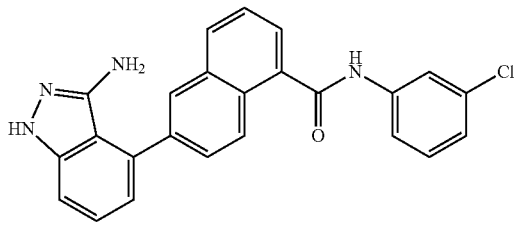 [SMILES: Nc1n[nH]c2cccc(-c3ccc4c(C(=O)Nc5cccc(Br)c5)cccc4c3)c12]

Step 1

N-(3-chlorophenyl)-6-(4,4,5,5-tetramethyl-1,3,2-dioxaborolan-2-yl)-1-naphthalenecarboxamide Phenylamine was replaced by 3-chlorophenylamine and other raw materials, reagents and preparation method were identical with those in step 4 of example 1 to give N-(3-chlorophenyl)-6-(4,4,5,5-tetramethyl-1,3,2-dioxaborolan-2-yl)-1-naphthalenecarboxamide as faint yellow solid.
$^1$H NMR (400 MHz, CDCl$_3$) δ (ppm): 1.40 (s, 12H), 7.16 (d, J=8.4 Hz, 1H), 7.30-7.34 (m, 1H), 7.50-7.54 (m, 2H), 7.70 (s, 1H), 7.77 (d, J=6.8 Hz, 1H), 7.86 (s, 1H), 7.93 (d, J=8.8 Hz, 1H), 8.02 (d, J=8.4 Hz, 1H), 8.31 (d, J=8.4 Hz, 1H), 8.42 (s, 1H).

Step 2

6-(3-amino-1H-indazol-4-yl)-N-(3-chlorophenyl)-1-naphthalenecarboxamide (I-15)

N-phenyl-6-(4,4,5,5-tetramethyl-1,3,2-dioxaborolan-2-yl)-1-naphthalenecarboxamide was replaced by N-(3-chlorophenyl)-6-(4,4,5,5-tetramethyl-1,3,2-dioxaborolan-2-yl)-1-naphthalenecarboxamide and other raw materials, reagents and preparation method were identical with those in step 6 of example 1 to give off-white solid I-15.
$^1$H NMR (400 MHz, DMSO-$d_6$) δ (ppm): 4.33 (s, 2H), 6.94 (t, J=4.0 Hz, 1H), 7.19-7.22 (m, 1H), 7.34-7.35 (m, 2H), 7.42 (t, J=8.0 Hz, 1H), 7.67-7.73 (m, 2H), 7.75 (dd, J=8.8, 2.0 Hz, 1H), 7.83 (dd, J=6.8, 0.8 Hz, 1H), 8.06 (t, J=2.0 Hz, 1H), 8.14 (d, J=1.6 Hz, 1H), 8.20 (d, J=8.4 Hz, 1H), 8.30 (d, J=8.4 Hz, 1H), 10.83 (s, 1H), 11.85 (s, 1H).

EXAMPLE 16

6-(3-amino-1H-indazol-4-yl)-N-(3-bromophenyl)-1-naphthalenecarboxamide (I-16)

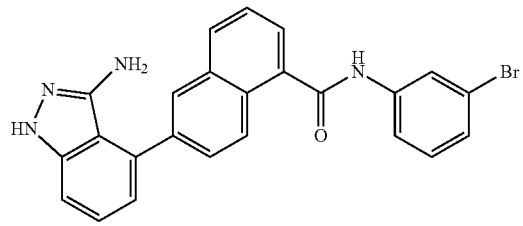

Step 1

N-(3-bromophenyl)-6-(4,4,5,5-tetramethyl-1,3,2-dioxaborolan-2-yl)-1-naphthalenecarboxamide Phenylamine was replaced by 3-bromophenylamine and other raw materials, reagents and preparation method were identical with those in step 4 of example 1 to give N-(3-bromophenyl)-6-(4,4,5,5-tetramethyl-1,3,2-dioxaborolan-2-yl)-1-naphthalenecarboxamide as faint yellow solid.
$^1$H NMR (400 MHz, CDCl$_3$) δ (ppm): 1.40 (s, 12H), 7.28 (m, 1H), 7.31-7.33 (m, 1H), 7.50-7.58 (m, 2H), 7.68 (s, 1H), 7.77 (d, J=6.8 Hz, 1H), 7.93 (d, J=8.4 Hz, 1H), 7.80-8.04 (m, 2H), 8.31 (d, J=8.4 Hz, 1H), 8.42 (s, 1H).

Step 2

6-(3-amino-1H-indazol-4-yl)-N-(3-bromophenyl)-1-naphthalenecarboxamide (I-16)

N-phenyl-6-(4,4,5,5-tetramethyl-1,3,2-dioxaborolan-2-yl)-1-naphthalenecarboxamide was replaced by N-(3-bromophenyl)-6-(4,4,5,5-tetramethyl-1,3,2-dioxaborolan-2-yl)-1-naphthalenecarboxamide and other raw materials, reagents and preparation method were identical with those in step 6 of example 1 to give off-white solid I-16.
$^1$H NMR (400 MHz, DMSO-$d_6$) δ (ppm): 4.32 (s, 2H), 6.94 (t, J=4.0 Hz, 1H), 7.32-7.38 (m, 4H), 7.66-7.70 (m, 1H), 7.74-7.76 (m, 2H), 7.83 (dd, J=6.8, 0.8 Hz, 1H), 8.14 (d, J=1.2 Hz, 1H), 8.19-8.21 (m, 2H), 8.30 (d, J=8.8 Hz, 1H), 10.82 (s, 1H), 11.85 (s, 1H).

EXAMPLE 17

6-(3-amino-1H-indazol-4-yl)-N-(3,5-dichlorophenyl)-1-naphthalenecarboxamide (I-17)

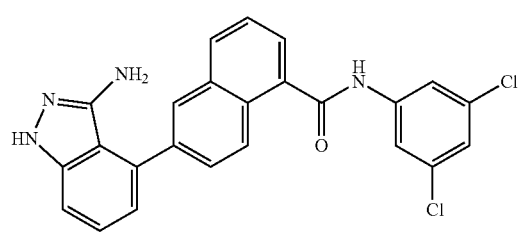 [SMILES: Nc1n[nH]c2cccc(-c3ccc4c(C(=O)Nc5cc(Cl)cc(Cl)c5)cccc4c3)c12]

Step 1

N-(3,5-dichlorophenyl)-6-(4,4,5,5-tetramethyl-1,3,2-dioxaborolan-2-yl)-1-naphthalenecarboxamide Phenylamine was replaced by 3,5-dichlorophenylamine and other raw materials, reagents and preparation method were identical with those in step 4 of example 1 to give N-(3,5-dichlorophenyl)-6-(4,4,5,5-tetramethyl-1,3,2-dioxaborolan-2-yl)-1-naphthalenecarboxamide as white solid.

$^1$H NMR (300 MHz, CDCl$_3$) δ (ppm): 1.40 (s, 12H), 7.18 (m, 1H), 7.49-7.54 (m, 1H), 7.67-7.76 (m, 4H), 7.93 (d, J=8.4 Hz, 1H), 8.03 (d, J=8.7 Hz, 1H), 8.29 (d, J=9.0 Hz, 1H), 8.41 (s, 1H).

Step 2

6-(3-amino-1H-indazol-4-yl)-N-(3,5-dichlorophenyl)-1-naphthalenecarboxamide (I-17)

N-phenyl-6-(4,4,5,5-tetramethyl-1,3,2-dioxaborolan-2-yl)-1-naphthalenecarboxamide was replaced by N-(3,5-dichlorophenyl)-6-(4,4,5,5-tetramethyl-1,3,2-dioxaborolan-2-yl)-1-naphthalenecarboxamide and other raw materials, reagents and preparation method were identical with those in step 6 of example 1 to give off-white solid I-17.

$^1$H NMR (400 MHz, DMSO-d$_6$) δ (ppm): 4.32 (s, 2H), 6.95 (t, J=4.0 Hz, 1H), 7.35-7.36 (m, 2H), 7.39 (t, J=2.0 Hz, 1H), 7.70 (dd, J=8.0, 7.2 Hz, 1H), 7.76 (dd, J=8.8, 2.0 Hz, 1H), 7.85 (dd, J=7.2, 1.2 Hz, 1H), 7.93-7.94 (m, 2H), 8.15 (d, J=1.6 Hz, 1H), 8.22 (d, J=8.4 Hz, 1H), 8.31 (d, J=8.4 Hz, 1H), 10.99 (s, 1H), 11.85 (s, 1H).

EXAMPLE 18

6-(3-amino-1H-indazol-4-yl)-N-(3,5-dibromophenyl)-1-naphthalenecarboxamide (I-18)

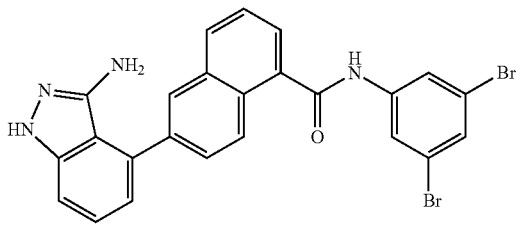 [SMILES: Nc1n[nH]c2cccc(-c3ccc4c(C(=O)Nc5cc(Br)cc(Br)c5)cccc4c3)c12]

Step 1

N-(3,5-dibromophenyl)-6-(4,4,5,5-tetramethyl-1,3,2-dioxaborolan-2-yl)-1-naphthalenecarboxamide Phenylamine was replaced by 3,5-dibromophenylamine and other raw materials, reagents and preparation method were identical with those in step 4 of example 1 to give N-(3,5-dibromophenyl)-6-(4,4,5,5-tetramethyl-1,3,2-dioxaborolan-2-yl)-1-naphthalenecarboxamide as off-white solid.

$^1$H NMR (400 MHz, CDCl$_3$) δ (ppm): 1.40 (s, 12H), 7.48 (s, 1H), 7.49-7.53 (m, 1H), 7.71 (s, 1H), 7.75 (d, J=7.2 Hz, 1H), 7.87 (s, 2H), 7.94 (d, J=8.8 Hz, 1H), 8.03 (d, J=8.4 Hz, 1H), 8.28 (d, J=8.0 Hz, 1H), 8.40 (s, 1H).

Step 2

6-(3-amino-1H-indazol-4-yl)-N-(3,5-dibromophenyl)-1-naphthalenecarboxamide (I-18)

N-phenyl-6-(4,4,5,5-tetramethyl-1,3,2-dioxaborolan-2-yl)-1-naphthalenecarboxamide was replaced by N-(3,5-dibromophenyl)-6-(4,4,5,5-tetramethyl-1,3,2-dioxaborolan-2-yl)-1-naphthalenecarboxamide and other raw materials, reagents and preparation method were identical with those in step 6 of example 1 to give white solid I-18.

$^1$H NMR (400 MHz, DMSO-d$_6$) δ (ppm): 4.32 (s, 2H), 6.94 (m, 1H), 7.34-7.35 (m, 2H), 7.61 (s, 1H), 7.67-7.71 (m, 1H), 7.75-7.77 (m, 1H), 7.84 (d, J=6.8 Hz, 1H), 8.11-8.15 (m, 3H), 8.22 (d, J=8.0 Hz, 1H), 8.31 (d, J=8.4 Hz, 1H), 10.94 (s, 1H), 11.84 (s, 1H).

EXAMPLE 19

6-(3-amino-1H-indazol-4-yl)-N-(3-(trifluoromethyl)phenyl)-1-naphthalenecarboxamide (I-19)

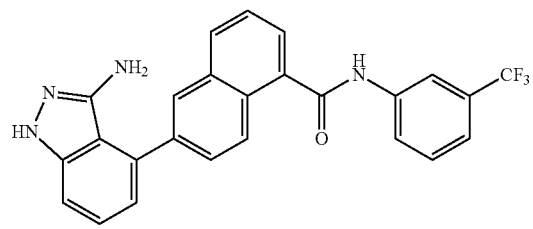 [SMILES: Nc1n[nH]c2cccc(-c3ccc4c(C(=O)Nc5cccc(C(F)(F)F)c5)cccc4c3)c12]

Step 1

6-(4,4,5,5-tetramethyl-1,3,2-dioxaborolan-2-yl)-N-(3-(trifluoromethyl)phenyl)-1-naphthalenecarboxamide Phenylamine was replaced by 3-trifluoromethylphenylamine and other raw materials, reagents and preparation method were identical with those in step 4 of example 1 to give 6-(4,4,5,5-tetramethyl-1,3,2-dioxaborolan-2-yl)-N-(3-(trifluoromethyl)phenyl)-1-naphthalenecarboxamide as yellow solid.

$^1$H NMR (400 MHz, CDCl$_3$) δ (ppm): 1.40 (s, 12H), 7.44 (d, J=7.6 Hz, 1H), 7.49-7.54 (m, 2H), 7.78 (d, J=7.2 Hz, 1H), 7.85 (s, 1H), 7.89-7.94 (m, 2H), 8.00-8.04 (m, 2H), 8.32 (d, J=8.8 Hz, 1H), 8.41 (s, 1H).

Step 2

6-(3-amino-1H-indazol-4-yl)-N-(3-(trifluoromethyl)phenyl)-1-naphthalenecarboxamide (I-19)

N-phenyl-6-(4,4,5,5-tetramethyl-1,3,2-dioxaborolan-2-yl)-1-naphthalenecarboxamide was replaced by 6-(4,4,5,5-tetramethyl-1,3,2-dioxaborolan-2-yl)-N-(3-(trifluoromethyl)phenyl)-1-naphthalenecarboxamide and other raw materials, reagents and preparation method were identical with those in step 6 of example 1 to give off-white solid I-19.

¹H NMR (400 MHz, DMSO-d₆) δ (ppm): 4.32 (s, 2H), 6.95 (t, J=4.0 Hz, 1H), 7.34-7.35 (m, 2H), 7.50 (d, J=7.6 Hz, 1H), 7.64 (t, J=8.0 Hz, 1H), 7.67-7.71 (m, 1H), 7.75 (dd, J=8.8, 2.0 Hz, 1H), 7.86 (dd, J=7.2, 1.2 Hz, 1H), 8.03 (d, J=8.0 Hz, 1H), 8.14 (d, J=1.6 Hz, 1H), 8.21 (d, J=8.4 Hz, 1H), 8.33 (d, J=8.8 Hz, 1H), 8.37 (s, 1H), 10.99 (s, 1H), 11.85 (s, 1H).

EXAMPLE 20

6-(3-amino-1H-indazol-4-yl)-N-(2-fluoro-5-methyl-phenyl)-1-naphthalenecarboxamide (I-20)

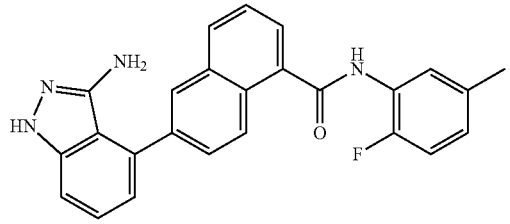 [SMILES: Cc1ccc(F)c(NC(=O)c2cccc3cc(-c4cccc5[nH]nc(N)c45)ccc23)c1]

Step 1

N-(2-fluoro-5-methylphenyl)-6-(4,4,5,5-tetramethyl-1,3,2-dioxaborolan-2-yl)-1-naphthalenecarboxamide Phenylamine was replaced by 2-fluoro-5-methylphenylamine and other raw materials, reagents and preparation method were identical with those in step 4 of example 1 to give N-(2-fluoro-5-methylphenyl)-6-(4,4,5,5-tetramethyl-1,3,2-dioxaborolan-2-yl)-1-naphthalenecarboxamide as tan solid.

¹H NMR (400 MHz, CDCl₃) δ (ppm): 1.40 (s, 12H), 2.41 (s, 3H), 6.91-6.93 (m, 1H), 7.00-7.04 (m, 1H), 7.51-7.55 (m, 1H), 7.81 (d, J=6.4 Hz, 1H), 7.87 (m, 1H), 7.94 (dd, J=8.4, 1.2 Hz, 1H), 8.03 (d, J=8.0 Hz, 1H), 8.37 (d, J=8.8 Hz, 1H), 8.41-8.42 (m, 2H).

Step 2

6-(3-amino-1H-indazol-4-yl)-N-(2-fluoro-5-methyl-phenyl)-1-naphthalenecarboxamide (I-20)

N-phenyl-6-(4,4,5,5-tetramethyl-1,3,2-dioxaborolan-2-yl)-1-naphthalenecarboxamide was replaced by N-(2-fluoro-5-methylphenyl)-6-(4,4,5,5-tetramethyl-1,3,2-dioxaborolan-2-yl)-1-naphthalenecarboxamide and other raw materials, reagents and preparation method were identical with those in step 6 of example 1 to give off-white solid I-20.

¹H NMR (400 MHz, DMSO-d₆) δ (ppm): 2.34 (s, 3H), 4.32 (s, 2H), 6.95 (t, J=4.0 Hz, 1H), 7.08-7.10 (m, 1H), 7.18-7.23 (m, 1H), 7.35-7.37 (m, 2H), 7.62 (d, J=6.4 Hz, 1H), 7.65-7.69 (m, 1H), 7.76 (dd, J=8.8, 2.0 Hz, 1H), 7.82 (d, J=6.8 Hz, 1H), 8.13 (d, J=1.6 Hz, 1H), 8.18 (d, J=8.0 Hz, 1H), 8.37 (d, J=8.8 Hz, 1H), 10.37 (s, 1H), 11.86 (s, 1H).

EXAMPLE 21

6-(3-amino-1H-indazol-4-yl)-N-(4-fluoro-3-methyl-phenyl)-1-naphthalenecarboxamide (I-21)

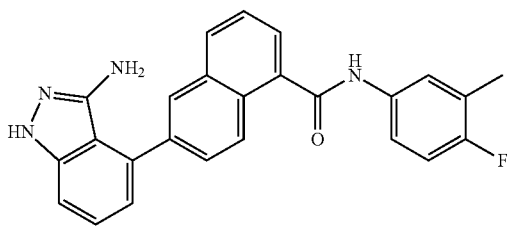 [SMILES: Cc1cc(NC(=O)c2cccc3cc(-c4cccc5[nH]nc(N)c45)ccc23)ccc1F]

Step 1

N-(4-fluoro-3-methylphenyl)-6-(4,4,5,5-tetramethyl-1,3,2-dioxaborolan-2-yl)-1-naphthalenecarboxamide Phenylamine was replaced by 4-fluoro-3-methylphenylamine and other raw materials, reagents and preparation method were identical with those in step 4 of example 1 to give N-(4-fluoro-3-methylphenyl)-6-(4,4,5,5-tetramethyl-1,3,2-dioxaborolan-2-yl)-1-naphthalenecarboxamide as off-white solid.

¹H NMR (300 MHz, CDCl₃) δ (ppm): 1.40 (s, 12H), 2.32 (d, J=0.6 Hz, 3H), 7.02 (t, J 9.0 Hz, 1H), 7.39-7.42 (m, 1H), 7.48-7.53 (m, 1H), 7.57-7.62 (m, 2H), 7.76 (d, J=7.2 Hz, 1H), 7.92 (d, J=8.4 Hz, 1H), 8.01 (d, J 7.8 Hz, 1H), 8.32 (d, J=8.4 Hz, 1H), 8.41 (s, 1H).

Step 2

6-(3-amino-1H-indazol-4-yl)-N-(4-fluoro-3-methyl-phenyl)-1-naphthalenecarboxamide (I-21)

N-phenyl-6-(4,4,5,5-tetramethyl-1,3,2-dioxaborolan-2-yl)-1-naphthalenecarboxamide was replaced by N-(4-fluoro-3-methylphenyl)-6-(4,4,5,5-tetramethyl-1,3,2-dioxaborolan-2-yl)-1-naphthalenecarboxamide and other raw materials, reagents and preparation method were identical with those in step 6 of example 1 to give off-white solid I-21.

¹H NMR (400 MHz, DMSO-d₆) δ (ppm): 2.27 (s, 3H), 4.32 (s, 2H), 6.94 (t, J=3.6 Hz, 1H), 7.16 (t, J=9.2 Hz, 1H), 7.34-7.35 (m, 2H), 7.61-7.69 (m, 2H), 7.73-7.80 (m, 3H), 8.13 (s, 1H), 8.18 (d, J=8.0 Hz, 1H), 8.29 (d, J=8.4 Hz, 1H), 10.62 (s, 1H), 11.84 (s, 1H).

EXAMPLE 22

6-(3-amino-1H-indazol-4-yl)-N-(2-fluoro-4-methyl-phenyl)-1-naphthalenecarboxamide (I-22)

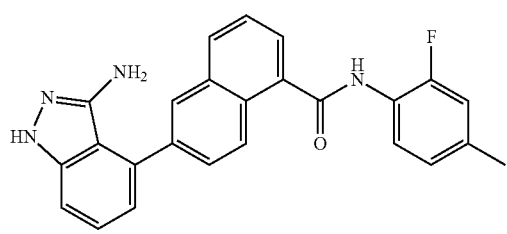

Step 1

N-(2-fluoro-4-methylphenyl)-6-(4,4,5,5-tetramethyl-1,3,2-dioxaborolan-2-yl)-1-naphthalenecarboxamide Phenylamine was replaced by 2-fluoro-4-methylphenylamine and other raw materials, reagents and preparation method were identical with those in step 4 of example 1 to give N-(2-fluoro-4-methylphenyl)-6-(4,4,5,5-tetramethyl-1,3,2-dioxaborolan-2-yl)-1-naphthalenecarboxamide as off-white solid.

$^1$H NMR (300 MHz, CDCl$_3$) δ (ppm): 1.40 (s, 12H), 2.63 (s, 3H), 6.94-7.05 (m, 2H), 7.50-7.55 (m, 1H), 7.78-7.82 (m, 2H), 7.93 (d, J=8.4 Hz, 1H), 8.02 (d, J=8.1 Hz, 1H), 8.36-8.44 (m, 3H).

Step 2

6-(3-amino-1H-indazol-4-yl)-N-(2-fluoro-4-methylphenyl)-1-naphthalenecarboxamide (I-22)

N-phenyl-6-(4,4,5,5-tetramethyl-1,3,2-dioxaborolan-2-yl)-1-naphthalene carb oxamide was replaced by N-(2-fluoro-4-m ethylphenyl)-6-(4,4,5,5-tetramethyl-1,3,2-dioxaborolan-2-yl)-1-naphthalenecarboxamide and other raw materials, reagents and preparation method were identical with those in step 6 of example 1 to give white solid I-22.

$^1$H NMR (400 MHz, DMSO-d$_6$) δ (ppm): 2.35 (s, 3H), 4.32 (s, 2H), 6.94 (t, J=4.0 Hz, 1H), 7.07 (d, J=8.0 Hz, 1H), 7.16 (d, J=11.6 Hz, 1H), 7.34-7.35 (m, 2H), 7.64-7.69 (m, 2H), 7.75 (d, J=8.8 Hz, 1H), 7.83 (d, =6.8 Hz, 1H), 8.12 (s, 1H), 8.18 (d, J=8.0 Hz, 1H), 8.37 (d, J=8.8 Hz, 1H), 10.32 (s, 1H), 11.85 (s, 1H).

EXAMPLE 23

6-(3-amino-1H-indazol-4-yl)-N-(3-fluoro-4-methylphenyl)-1-naphthalenecarboxamide (I-23)

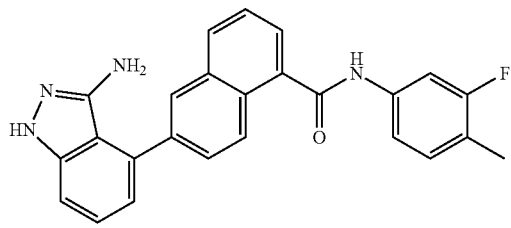 [SMILES: Cc1ccc(NC(=O)c2cccc3cc(-c4cccc5[nH]nc(N)c45)ccc23)cc1F]

Step 1

N-(3-fluoro-4-methylphenyl)-6-(4,4,5,5-tetramethyl-1,3,2-dioxaborolan-2-yl)-1-naphthalenecarboxamide Phenylamine was replaced by 3-fluoro-4-methylphenylamine and other raw materials, reagents and preparation method were identical with those in step 4 of example 1 to give N-(3-fluoro-4-methylphenyl)-6-(4,4,5,5-tetramethyl-1,3,2-dioxaborolan-2-yl)-1-naphthalenecarboxamide as off-white solid.

$^1$H NMR (300 MHz, CDCl$_3$) δ (ppm): 1.40 (s, 12H), 2.27 (d, J=1.8 Hz, 3H), 7.17-7.18 (m, 2H), 7.48-7.53 (m, 1H), 7.61-7.66 (m, 2H), 7.76 (d, J=7.2 Hz, 1H), 7.92 (dd, J=8.7, 1.5 Hz, 1H), 8.01 (d, J=8.4 Hz, 1H), 8.32 (d, J=8.7 Hz, 1H), 8.41 (s, 1H).

Step 2

6-(3-amino-1H-indazol-4-yl)-N-(3-fluoro-4-methylphenyl)-1-naphthalenecarboxamide (I-23)

N-phenyl-6-(4,4,5,5-tetramethyl-1,3,2-dioxaborolan-2-yl)-1-naphthalenecarboxamide was replaced by N-(3-fluoro-4-methylphenyl)-6-(4,4,5,5-tetramethyl-1,3,2-dioxaborolan-2-yl)-1-naphthalenecarboxamide and other raw materials, reagents and preparation method were identical with those in step 6 of example 1 to give white solid I-23.

$^1$H NMR (400 MHz, DMSO-d$_6$) δ (ppm): 2.23 (s, 3H), 4.32 (s, 2H), 6.94 (t, J=4.0 Hz, 1H), 7.28 (t, J=8.4 Hz, 1H), 7.34-7.35 (m, 2H), 7.46-7.48 (m, 1H), 7.68 (t, J=7.6 Hz, 1H), 7.74-7.81 (m, 3H), 8.13 (s, 1H), 8.19 (d, J=8.4 Hz, 1H), 8.29 (d, J=8.8 Hz, 1H), 10.75 (s, 1H), 11.85 (s, 1H).

EXAMPLE 24

6-(3-amino-1H-indazol-4-yl)-N-(5-methylisoxazol-3-yl)-1-naphthalenecarboxamide (I-24)

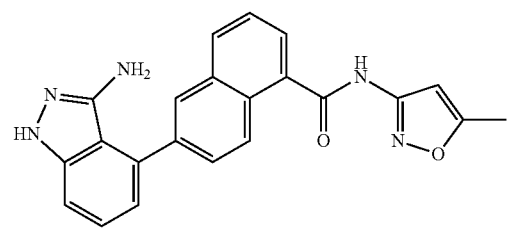 [SMILES: Cc1cc(NC(=O)c2cccc3cc(-c4cccc5[nH]nc(N)c45)ccc23)no1]

Step 1

N-(5-methyl isoxazol-3-yl)-6-(4,4,5,5-tetramethyl-1,3,2-dioxaborolan-2-yl)-1-naphthalenecarboxamide Phenylamine was replaced by 5-methylisoxazolamine and other raw materials, reagents and preparation method were identical with those in step 4 of example 1 to give N-(5-methyl isoxazol-3-yl)-6-(4,4,5,5-tetramethyl-1,3,2-dioxaborolan-2-yl)-1-naphthalenecarboxamide as white solid.

$^1$H NMR (400 MHz, CDCl$_3$) δ (ppm): 1.40 (s, 12H), 2.47 (s, 3H), 6.95 (s, 1H), 7.50-7.54 (m, 1H), 7.82 (dd, J=7.2, 1.2 Hz, 1H), 7.94 (dd, J=8.4, 1.2 Hz, 1H), 8.05 (d, J=8.0, 1H), 8.35 (d, J=8.8 Hz, 1H), 8.42 (s, 1H), 8.50 (s, 1H).

Step 2

6-(3-amino-1H-indazol-4-yl)-N-(5-methylisoxazol-3-yl)-1-naphthalenecarboxamide (I-24)

N-phenyl-6-(4,4,5,5-tetramethyl-1,3,2-dioxaborolan-2-yl)-1-naphthalenecarboxamide was replaced by N-(5-methylisoxazol-3-yl)-6-(4,4,5,5-tetramethyl-1,3,2-dioxaborolan-2-yl)-1-naphthalenecarboxamide and other raw materials, reagents and preparation method were identical with those in step 6 of example 1 to give white solid I-24.

$^1$H NMR (400 MHz, DMSO-d$_6$) δ (ppm): 2.46 (s, 3H), 4.32 (s, 2H), 6.87 (s, 1H), 6.95 (t, J=3.6 Hz, 1H), 7.35-7.36 (m, 2H), 7.66 (dd, J=8.0, 7.2 Hz, 1H), 7.76 (dd, J=8.4, 1.6 Hz, 1H), 7.84 (dd, J=7.2, 0.8 Hz, 1H), 8.14 (d, J=1.6 Hz, 1H), 8.20 (d, J=8.4 Hz, 1H), 8.31 (d, J=8.8 Hz, 1H), 11.58 (s, 1H), 11.85 (s, 1H).

EXAMPLE 25

6-(3-amino-1H-indazol-4-yl)-N-(pyridin-3-yl)-1-naphthalenecarboxamide (I-25)

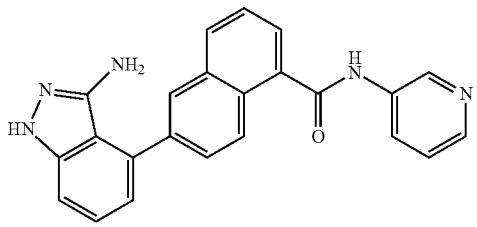 [SMILES: Nc1n[nH]c2cccc(-c3ccc4c(C(=O)Nc5cccnc5)cccc4c3)c12]

Step 1

N-(pyridin-3-yl)-6-(4,4,5,5-tetramethyl-1,3,2-dioxaborolan-2-yl)-1-naphthalenecarboxamide Phenylamine was replaced by 3-aminopyridine and other raw materials, reagents and preparation method were identical with those in step 4 of example 1 to give N-(pyridin-3-yl)-6-(4,4,5,5-tetramethyl-1,3,2-dioxaborolan-2-yl)-1-naphthalenecarboxamide as white solid.
$^1$H NMR (300 MHz, CDCl$_3$) δ (ppm): 1.40 (s, 12H), 7.35-7.39 (m, 1H), 7.51-7.56 (m, 1H), 7.75 (s, 1H), 7.80-7.82 (m, 1H), 7.94 (dd, J=8.4, 1.2 Hz, 1H), 8.04 (d, J=8.4 Hz, 1H), 8.32 (d, J=8.4 Hz, 1H), 8.40-8.44 (m, 3H), 8.67 (d, J=2.1 Hz, 1H).

Step 2

6-(3-amino-1H-indazol-4-yl)-N-(pyridin-3-yl)-1-naphthalenecarboxamide (I-25)

N-phenyl-6-(4,4,5,5-tetramethyl-1,3,2-dioxaborolan-2-yl)-1-naphthalenecarboxamide was replaced by N-(pyridin-3-yl)-6-(4,4,5,5-tetramethyl-1,3,2-dioxaborolan-2-yl)-1-naphthalene carboxamide and other raw materials, reagents and preparation method were identical with those in step 6 of example 1 to give faint yellow solid I-25.
$^1$H NMR (400 MHz, DMSO-d$_6$) δ (ppm): 4.32 (s, 2H), 6.95 (t, J=4.0 Hz, 1H), 7.35-7.36 (m, 2H), 7.43-7.47 (m, 1H), 7.68-7.72 (m, 1H), 7.76 (dd, J=8.8, 2.0 Hz, 1H), 7.87 (dd, J=7.2, 0.8 Hz, 1H), 8.15 (d, J=1.6 Hz, 1H), 8.21 (d, J=8.4 Hz, 1H), 8.28-8.30 (m, 1H), 8.33-8.36 (m, 2H), 8.98 (d, J=2.4 Hz, 1H), 10.87 (s, 1H), 11.85 (s, 1H).

EXAMPLE 26

6-(3-amino-1H-indazol-4-yl)-N-ethyl-1-naphthalenecarboxamide (I-26)

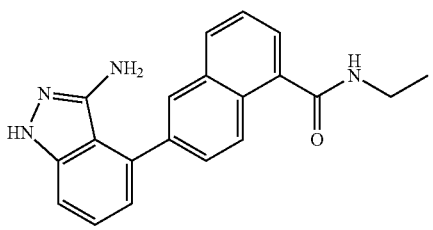 [SMILES: CCNC(=O)c1cccc2cc(-c3cccc4[nH]nc(N)c34)ccc12]

Step 1

N-ethyl-6-(4,4,5,5-tetramethyl-1,3,2-dioxaborolan-2-yl)-1-naphthalenecarboxamide Phenylamine was replaced by ethylamine (2 mol/L, in tetrahydrofuran) and other raw materials, reagents and preparation method were identical with those in step 4 of example 1 to give N-ethyl-6-(4,4,5,5-tetramethyl-1,3,2-dioxaborolan-2-yl)-1-naphthalenecarboxamide as white solid.
$^1$H NMR (400 MHz, CDCl$_3$) δ (ppm): 1.31 (t, J=7.2 Hz, 3H), 1.40 (s, 12H), 3.56-3.63 (m, 2H), 5.96 (m, 1H), 7.45 (dd, J=8.4, 7.2 Hz, 1H), 7.63 (dd, J=7.2, 1.2 Hz, 1H), 7.90 (dd, J=8.4, 1.2 Hz, 1H), 7.95 (d, J=8.4 Hz, 1H), 8.26 (d, J=8.8 Hz, 1H), 8.38 (s, 1H).

Step 2

6-(3-amino-1H-indazol-4-yl)-N-ethyl-1-naphthalenecarboxamide (I-26)

N-phenyl-6-(4,4,5,5-tetramethyl-1,3,2-dioxaborolan-2-)-1-naphthalenecarboxamide was replaced by N-ethyl-6-(4,4,5,5-tetramethyl-1,3,2-dioxaborolan-2-yl)-1-naphthalene carboxamide and other raw materials, reagents and preparation method were identical with those in step 6 of example 1 to give white solid I-26.
$^1$H NMR (400 MHz, DMSO-d$_6$) δ (ppm): 1.20 (t, J=7.2 Hz, 3H), 3.40 (m, 2H), 4.30 (s, 2H), 6.92-6.94 (m, 1H), 7.34-7.35 (m, 2H), 7.58-7.64 (m, 2H), 7.71 (dd, J=8.8, 2.0 Hz, 1H), 8.08 (d, J=2.0 Hz, 1H), 8.10 (dd, J=8.0, 2.0 Hz, 1H), 8.31 (d, J=8.8 Hz, 1H), 8.60 (t, J=5.6 Hz, 1H), 11.83 (s, 1H).

EXAMPLE 27

6-(3-amino-1H-indazol-4-yl)-N-cyclopropyl-1-naphthalenecarboxamide (I-27)

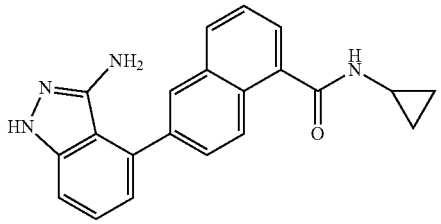 [SMILES: Nc1n[nH]c2cccc(-c3ccc4c(C(=O)NC5CC5)cccc4c3)c12]

Step 1

N-cyclopropyl-6-(4,4,5,5-tetramethyl-1,3,2-dioxaborolan-2-yl)-1-naphthalenecarboxamide Phenylamine was replaced by cyclopropylamine and other raw materials, reagents and preparation method were identical with those in step 4 of example 1 to give N-cyclopropyl-6-(4,4,5,5-tetramethyl-1,3,2-dioxaborolan-2-yl)-1-naphthalenecarboxamide as white solid.
$^1$H NMR (300 MHz, CDCl$_3$) δ (ppm): 0.67-0.70 (m, 2H), 0.90-0.94 (m, 2H), 1.39 (s, 12H), 3.01-3.04 (m, 1H), 6.08 (s, 1H), 7.41-7.46 (m, 1H), 7.59-7.61 (m, 1H), 7.89-7.96 (m, 2H), 8.26 (d, J=8.4 I-17, 114), 8.37 (s, 1H).

Step 2

6-(3-amino-1H-indazol-4-yl)-N-cyclopropyl-1-naphthalenecarboxamide (I-27)

N-phenyl-6-(4,4,5,5-tetramethyl-1,3,2-dioxaborolan-2-yl)-1-naphthalenecarboxamide was replaced by N-cyclopropyl-6-(4,4,5,5-tetramethyl-1,3,2-dioxaborolan-2-yl)-1-naphthalene carboxamide and other raw materials, reagents and preparation method were identical with those in step 6 of example 1 to give off-white solid I-27.

$^1$H NMR (400 MHz, DMSO-$d_6$) δ (ppm): 0.61-0.63 (m, 2H), 0.74-0.76 (m, 2H), 2.97 (m, 1H), 4.30 (s, 2H), 6.93 (t, J=4.0 Hz, 1H), 7.34-7.35 (m, 2H), 7.58-7.60 (m, 2H), 7.71 (dd, J=8.8, 2.0 Hz, 1H), 8.07 (d, J=1.6 Hz, 1H), 8.09 (dd, J=6.4, 2.4 Hz, 1H), 8.30 (d, J=8.4 Hz, 1H), 8.64 (d, J=4.4 Hz, 1H), 11.84 (s, 1H).

EXAMPLE 28

6-(3-amino-1H-indazol-4-yl)-5-fluoro-N-phenyl-1-naphthalenecarboxamide (I-28)

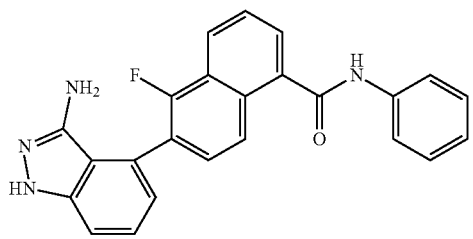 [SMILES: Nc1n[nH]c2cccc(-c3ccc4c(C(=O)Nc5ccccc5)cccc4c3F)c12]

Step 1 methyl 5-fluoro-6-hydroxy-1-naphthoate 1 g of methyl 6-hydroxy-1-naphthoate was dissloved in 10 ml of acetonitrile and 1.92 g of 1-chloromethyl-4-fluoro-1,4-diazabicyclo[2.2.2]octane bis(tetrafluoroborate) was added and heated to 85° C. After stirred for 24 h, the mixture was cooled to room temperature and then concentrated. The residue was purified by column chromatography (dichloromethane) to give 593 mg of methyl 5-fluoro-6-hydroxy-1-naphthoate as yellow solid. Yield: 54%.

$^1$H NMR (300 MHz, DMSO-$d_6$) δ (ppm): 3.92 (s, 3H), 7.40 (t, J=9.0 Hz, 1H), 7.59-7.64 (m, 1H), 7.98 (d, J=7.2 Hz, 1H), 8.17 (d, J 8.4 Hz, 1H), 8.43 (d, J=9.3 Hz, 1H), 10.34 (s, 1H).

Step 2 methyl 5-fluoro-6-(((trifluoromethyl)sulfonyl)oxy)-1-naphthoate

Methyl 6-hydroxy-1-naphthoate was replaced by methyl 5-fluoro-6-hydroxy-1-naphthoate and other raw materials, reagents and preparation method were identical with those in step 1 of example 1 to give methyl 5-fluoro-6-(((trifluoromethyl)sulfonyl)oxy)-1-naphthoate as pale yellow oil.

$^1$H NMR (300 MHz, DMSO-$d_6$) δ (ppm): 3.98 (s, 3H), 7.86-7.97 (m, 2H), 8.36 (dd, J=7.2, 0.9 Hz, 1H), 8.47 (d, J=8.4 Hz, 1H), 8.75 (dd, J 9.6, 0.6 Hz, 1H).

Step 3 methyl 5-fluoro-6-(4,4,5,5-tetramethyl-1,3,2-dioxaborolan-2-yl)-1-naphthoate Methyl 6-(((trifluoromethyl)sulfonyl)oxy)-1-naphthoate was replaced by methyl 5-fluoro-6-(((trifluoromethyl)sulfonyl)oxy)-1-naphthoate and other raw materials, reagents and preparation method were identical with those in step 2 of example 1 to give methyl 5-fluoro-6-(4,4,5,5-tetramethyl-1,3,2-dioxaborolan-2-yl)-1-naphthoate as white solid.

$^1$H NMR (300 MHz, CDCl$_3$) δ (ppm): 1.41 (s, 12H), 4.01 (s, 3H), 7.56 (dd, J=8.4, 7.8 Hz, 1H), 7.84 (dd, J=8.4, 6.0 Hz, 1H), 8.27 (dd, J=7.5, 1.2 Hz, 1H), 8.38 (d, J=8.4 Hz, 1H), 8.66 (dd, J=8.7, 0.9 Hz, 1H).

Step 4

5-fluoro-6-(4,4,5,5-tetramethyl-1,3,2-dioxaborolan-2-yl)-1-naphthoic acid

Methyl 6-(4,4,5,5-tetramethyl-1,3,2-dioxaborolan-2-yl)-1-naphthoate was replaced by methyl 5-fluoro-6-(4,4,5,5-tetramethyl-1,3,2-dioxaborolan-2-yl)-1-naphthoate and other raw materials, reagents and preparation method were identical with those in step 3 of example 1 to give 5-fluoro-6-(4,4,5,5-tetramethyl-1,3,2-dioxaborolan-2-yl)-1-naphthoic acid as white solid.

$^1$H NMR (300 MHz, DMSO-$d_6$) δ (ppm): 1.35 (s, 12H), 7.70-7.78 (m, 2H), 8.28 (dd, J=7.5, 1.2 Hz, 1H), 8.34 (d, J=8.1 Hz, 1H), 8.66 (d, J=9.0 Hz, 1H).

Step 5

5-fluoro-N-phenyl-6-(4,4,5,5-tetramethyl-1,3,2-dioxaborolan-2-yl)-1-naphthalenecarboxamide 6-(4,4,5,5-tetramethyl-1,3,2-dioxaborolan-2-yl)-1-naphthoic acid was replaced by 5-fluoro-6-(4,4,5,5-tetramethyl-1,3,2-dioxaborolan-2-yl)-1-naphthoic acid and other raw materials, reagents and preparation method were identical with those in step 4 of example 1 to give 5-fluoro-N-phenyl-6-(4,4,5,5-tetramethyl-1,3,2-dioxaborolan-2-yl)-1-naphtha 1 ene carboxamide as yellow solid.

$^1$H NMR (300 MHz, CDCl$_3$) δ (ppm): 1.41 (s, 12H), 7.20 (t, J=7.2 Hz, 1H), 7.41 (t, J=7.8 Hz, 2H), 7.53-7.58 (m, 1H), 7.68-7.72 (m, 3H), 7.77-7.83 (m, 2H), 8.09 (d, J=8.4 Hz, 1H), 8.29 (d, J=8.4 Hz, 1H).

Step 6

6-(3-amino-1H-indazol-4-yl)-5-fluoro-N-phenyl-1-naphthalenecarboxamide (I-28)

N-phenyl-6-(4,4,5,5-tetramethyl-1,3,2-dioxaborolan-2-yl)-1-naphthalenecarboxamide was replaced by 5-fluoro-N-phenyl-6-(4,4,5,5-tetramethyl-1,3,2-dioxaborolan-2-yl)-1-naphthalene carboxamide and other raw materials, reagents and preparation method were identical with those in step 6 of example 1 to give brown solid I-28.

$^1$H NMR (300 MHz, DMSO-$d_6$) δ (ppm): 4.19 (s, 2H), 6.94 (dd, J=5.7, 2.1 Hz, 1H), 7.12-7.17 (m, 1H), 7.33-7.42 (m, 4H), 7.61-7.66 (m, 1H), 7.77-7.84 (m, 3H), 7.90-7.92 (m, 1H), 8.12 (d, J=8.7 Hz, 1H), 8.29 (d, J=8.4 Hz, 1H), 10.69 (s, 1H), 11.88 (s, 1H).

EXAMPLE 29

6-(3-amino-1-methyl-1H-indazol-4-yl)-N-phenyl-1-naphthalenecarboxamide (I-29)

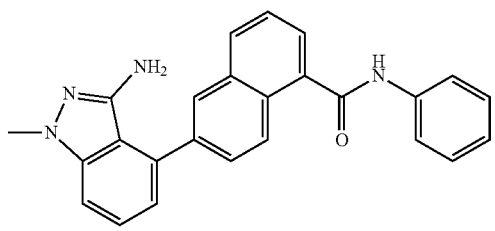 [SMILES: Cn1nc(N)c2c(-c3ccc4c(C(=O)Nc5ccccc5)cccc4c3)cccc21]

Step 1

4-iodo-1-methyl-1H-indazol-3-amine

Hydrazine hydrate was replaced by methylhydrazine and other raw materials, reagents and preparation method were identical with those in step 5 of example 1 to give 4-iodo-1-methyl-1H-indazol-3-amine as yellow solid.

$^1$H NMR (300 MHz, DMSO-$d_6$) δ (ppm): 3.74 (s, 3H), 5.12 (s, 2H), 6.97 (dd, J=8.4, 7.5 Hz, 1H), 7.34 (d, J=7.8 Hz, 1H), 7.40 (d, J=8.4 Hz, 1H).

Step 2

6-(3-amino-1-methyl-1H-indazol-4-yl)-N-phenyl-1-naphthalenecarboxamide (I-29)

4-iodo-1H-indazol-3-amine was replaced by 4-iodo-1-methyl-1H-indazol-3-amine and other raw materials, reagents and preparation method were identical with those in step 6 of example 1 to give yellow solid I-29.

$^1$H NMR (300 MHz, DMSO-$d_6$) δ (ppm): 3.83 (s, 3H), 4.38 (s, 2H), 6.96 (d, J=6.9 Hz, 1H), 7.14 (t, J=7.5 Hz, 1H), 7.37-7.47 (m, 4H), 7.68-7.75 (m, 2H), 7.80-7.85 (m, 3H), 8.13 (s, 1H), 8.19 (d, J=8.4 Hz, 1H), 8.31 (d, J=8.7 Hz, 1H), 10.64 (s, 1H).

EXAMPLE 30

6-(3-amino-1H-indazol-4-yl)-N-phenyl-2-naphthalenecarboxamide (I-30)

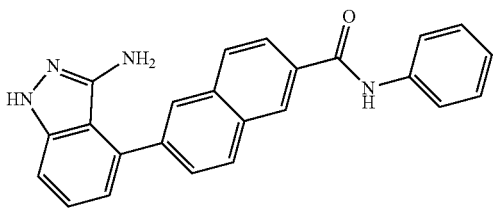 [SMILES: Nc1n[nH]c2cccc(-c3ccc4cc(C(=O)Nc5ccccc5)ccc4c3)c12]

Step 1 methyl 6-(trifluoromethylsulfonyloxy)-2-naphthoate 6-hydroxy-1-naphthoic acid was replaced by 6-hydroxy-2-naphthoic acid and other raw materials, reagents and preparation method were identical with those in step 1 of example 1 to give methyl 6-(trifluoromethylsulfonyloxy)-2-naphthoate as yellow solid.

$^1$H NMR (300 MHz, CDCl$_3$) δ (ppm): 4.01 (s, 3H), 7.45 (dd, J=9.0, 2.4 Hz, 1H), 7.80 (d, J=2.4 Hz, 1H), 7.94 (d, J=8.4 Hz, 1H), 8.06 (d, J=9.3 Hz, 1H), 8.17 (dd, J=8.4, 1.2 Hz, 1H), 8.66 (s, 1H).

Step 2 methyl 6-(4,4,5,5-tetramethyl-1,3,2-dioxaborolan-2-yl)-2-naphthoate

Methyl 6-(trifluoromethylsulfonyloxy)-1-naphthoate was replaced by methyl 6-(trifluoromethylsulfonyloxy)-2-naphthoate and other raw materials, reagents and preparation method were identical with those in step 2 of example 1 to give methyl 6-(4,4,5,5-tetramethyl-1,3,2-dioxaborolan-2-yl)-2-naphthoate as white solid.

$^1$H NMR (300 MHz, CDCl$_3$) δ (ppm): 1.40 (s, 12H), 3.98 (s, 3H), 7.88-7.95 (m, 3H), 8.06 (d, J=8.4 Hz, 1H), 8.40 (s, 1H), 8.60 (s, 1H).

Step 3

6-(4,4,5,5-tetramethyl-1,3,2-dioxaborolan-2-yl)-2-naphthoic acid

Methyl 6-(4,4,5,5-tetramethyl-1,3,2-dioxaborolan-2-yl)-1-naphthoate was replaced by methyl 6-(4,4,5,5-tetramethyl-1,3,2-dioxaborolan-2-yl)-2-naphthoate and other raw materials, reagents and preparation method were identical with those in step 3 of example 1 to give 6-(4,4,5,5-tetramethyl-1,3,2-dioxaborolan-2-yl)-2-naphthoic acid as white solid.

$^1$H NMR (300 MHz, DMSO-$d_6$) δ (ppm): 1.34 (s, 12H), 7.78 (d, J=8.1 Hz, 1H), 7.98 (dd, J=8.7, 1.5 Hz, 1H), 8.08-8.13 (m, 2H), 8.38 (s, 1H), 8.60 (s, 1H), 13.15 (s, 1H).

Step 4

N-phenyl-6-(4,4,5,5-tetramethyl-1,3,2-dioxaborolan-2-yl)-2-naphthalenecarboxamide 6-(4,4,5,5-tetramethyl-1,3,2-dioxaborolan-2-yl)-1-naphthoic acid was replaced by 6-(4,4,5,5-tetramethyl-1,3,2-dioxaborolan-2-yl)-2-naphthoic acid and other raw materials, reagents and preparation method were identical with those in step 4 of example 1 to give N-phenyl-6-(4,4,5,5-tetramethyl-1,3,2-dioxaborolan-2-yl)-2-naphthalenecarboxamide as orange jelly.

$^1$H NMR (300 MHz, CDCl$_3$) δ (ppm): 1.41 (s, 12H), 7.16-7.26 (m, 1H), 7.41 (t, J=7.8 Hz, 2H), 7.70 (d, J=8.1 Hz, 2H), 7.91-8.01 (m, 5H), 8.37 (s, 1H), 8.42 (s, 1H).

Step 5

6-(3-amino-1H-indazol-4-yl)-N-phenyl-2-naphthalenecarboxamide (I-30)

N-phenyl-6-(4,4,5,5-tetramethyl-1,3,2-dioxaborolan-2-yl)-1-naphthalenecarboxamide was replaced by N-phenyl-6-(4,4,5,5-tetramethyl-1,3,2-dioxaborolan-2-yl)-2-naphthalene carboxamide and other raw materials, reagents and preparation method were identical with those in step 6 of example 1 to give yellow solid I-30.

¹H NMR (300 MHz, DMSO-d₆) δ (ppm): 4.33 (s, 2H), 6.96-6.98 (m, 1H), 7.13 (t, J=7.5 Hz, 1H), 7.35-7.42 (m, 4H), 7.76 (d, J=8.4 Hz, 1H), 7.85 (d, J=7.5 Hz, 2H), 8.07-8.17 (m, 3H), 8.22 (d, J=8.4 Hz, 1H), 8.67 (s, 1H), 10.48 (s, 1H), 11.86 (s, 1H).

EXAMPLE 31

6-(3-amino-1H-indazol-4-yl)-5-fluoro-N-phenyl-2-naphthalenecarboxamide (I-31)

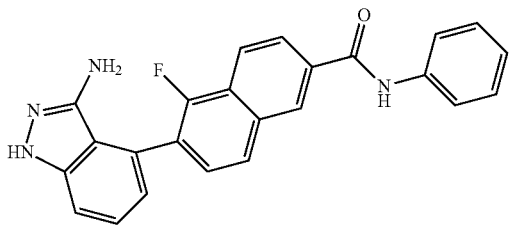 [SMILES: Nc1n[nH]c2cccc(-c3ccc4cc(C(=O)Nc5ccccc5)ccc4c3F)c12]

Step 1 methyl 5-fluoro-6-hydroxy-2-naphthoate

Methyl 6-hydroxy-1-naphthoate was replaced by methyl 6-hydroxy-2-naphthoate and other raw materials, reagents and preparation method were identical with those in step 1 of example 28 to give methyl 5-fluoro-6-hydroxy-2-naphthoate as yellow solid.

¹H NMR (300 MHz, DMSO-d₆) δ (ppm): 3.90 (s, 3H), 7.35 (t, J=8.7 Hz, 1H), 7.87 (d, J=9.0 Hz, 1H), 7.94-7.98 (m, 2H), 8.58 (s, 1H), 10.58 (s, 1H).

Step 2 methyl 5-fluoro-6-(((trifluoromethyl)sulfonyl)oxy)-2-naphthoate

Methyl 6-hydroxy-1-naphthoate was replaced by methyl 5-fluoro-6-hydroxy-2-naphthoate and other raw materials, reagents and preparation method were identical with those in step 1 of example 1 to give methyl 5-fluoro-6-(((trifluoromethyl)sulfonyl)oxy)-2-naphthoate as yellow solid.

¹H NMR (300 MHz, CDCl₃) δ (ppm): 4.02 (s, 3H), 7.48 (dd, J=9.0, 6.9 Hz, 1H), 7.84 (dd, J=9.0, 1.5 Hz, 1H), 8.19-8.26 (m, 2H), 8.66 (s, 1H).

Step 3 methyl 5-fluoro-6-(4,4,5,5-tetramethyl-1,3,2-dioxaborolan-2-yl)-2-naphthoate

Methyl 6-(((trifluoromethyl)sulfonyl)oxy)-1-naphthoate was replaced by methyl 5-fluoro-6-((((trifluoromethyl)sulfonyl)oxy)-2-naphthoate and other raw materials, reagents and preparation method were identical with those in step 2 of example 1 to give methyl 5-fluoro-6-(4,4,5,5-tetramethyl-1,3,2-dioxaborolan-2-yl)-2-naphthoate as yellow solid.

Step 4

5-fluoro-6-(4,4,5,5-tetramethyl-1,3,2-dioxaborolan-2-yl)-2-naphthoic acid

Methyl 6-(4,4,5,5-tetramethyl-1,3,2-dioxaborolan-2-yl)-1-naphthoate was replaced by methyl 5-fluoro-6-(4,4,5,5-tetramethyl-1,3,2-dioxaborolan-2-yl)-2-naphthoate and other raw materials, reagents and preparation method were identical with those in step 3 of example 1 to give 5-fluoro-6-(4,4,5,5-tetramethyl-1,3,2-dioxaborolan-2-yl)-2-naphthoic acid as white solid.

Step 5

5-fluoro-N-phenyl-6-(4,4,5,5-tetramethyl-1,3,2-dioxaborolan-2-yl)-2-naphthalenecarboxamide 6-(4,4,5,5-tetramethyl-1,3,2-dioxaborolan-2-yl)-1-naphthoic acid was replaced by 5-fluoro-6-(4,4, 5,5-tetramethyl-1,3,2-dioxaborolan-2-yl)-2-naphthoic acid and other raw materials, reagents and preparation method were identical with those in step 4 of example 1 to give 5-fluoro-N-phenyl-6-(4,4,5,5-tetramethyl-1,3,2-dioxaborolan-2-yl)-2-naphthalene carboxamide as yellow solid.

Step 6

6-(3-amino-1H-indazol-4-yl)-5-fluoro-N-phenyl-2-naphthalenecarboxamide (I-31)

N-phenyl-6-(4,4,5,5-tetramethyl-1,3,2-dioxaborolan-2-yl)-1-naphthalenecarboxamide was replaced by 5-fluoro-N-phenyl-6-(4,4,5,5-tetramethyl-1,3,2-dioxaborolan-2-yl)-2-naphthalene carboxamide and other raw materials, reagents and preparation method were identical with those in step 6 of example 1 to give brown solid I-31.

¹H NMR (300 MHz, DMSO-d₆) δ (ppm): 4.21 (s, 2H), 6.96 (d, J=6.0 Hz, 1H), 7.14 (t, J=7.5 Hz, 1H), 7.36-7.43 (m, 4H), 7.64 (t, J=8.1 Hz, 1H), 7.85 (d, J=8.4 Hz, 2H), 8.07 (d, J=8.4 Hz, 1H), 8.18 (d, J=8.4 Hz, 1H), 8.26 (d, J=9.0 Hz, 1H), 8.74 (s, 1H), 10.55 (s, 1H), 11.85 (s, 1H).

EXAMPLE 32

6-(3-amino-1H-indazol-4-yl)-5-chloro-N-phenyl-1-naphthalenecarboxamide (I-32)

Step 1 methyl 5-chloro-6-hydroxy-1-naphthoate 1 g of methyl 6-hydroxy-1-naphthoate and 762 mg of N-chlorosuccinimide were dissloved in 100 ml of tetrahydrofuran and stirred at room temperature for 5 h, then concentrated. The residue was purified by column chromatography (ethyl acetate:petroleum ether=10:90) to give 1.17 g of methyl 5-chloro-6-hydroxy-1-naphthoate as white solid. Yield: 100%.

¹H NMR (300 MHz, DMSO-d6) δ (ppm): 3.93 (s, 3H), 7.43 (d, J=9.3 Hz, 1H), 7.67 (dd, J=8.1, 7.2 Hz, 1H), 7.96 (d, J=7.5 Hz, 1H), 8.32 (d, J=8.4 Hz, 1H), 8.57 (d, J=9.3 Hz, 1H), 10.73 (s, 1H).

Step 2 methyl 5-chloro-6-(((trifluoromethyl)sulfonyl)oxy)-1-naphthoate

Methyl 6-hydroxy-1-naphthoate was replaced by methyl 5-chloro-6-hydroxy-1-naphthoate and other raw materials, reagents and preparation method were identical with those in step 1 of example 1 to give methyl 5-chloro-6-(((trifluoromethyl)sulfonyl)oxy)-1-naphthoate as faint yellow solid.

$^1$H NMR (300 MHz, CDCl$_3$) δ (ppm): 4.03 (s, 3H), 7.56 (d, J=9.6 Hz, 1H), 7.71-7.77 (m, 1H), 8.33 (dd, J=7.2, 0.9 Hz, 1H), 8.58 (d, J=8.4 Hz, 1H), 9.05 (d, J=9.0 Hz, 1H).

Step 3 methyl 5-chloro-6-(4,4,5,5-tetramethyl-1,3,2-dioxaborolan-2-yl)-1-naphthoate Methyl 6-(((trifluoromethyl)sulfonyl)oxy)-1-naphthoate was replaced by methyl 5-chloro-6-(((trifluoromethyl)sulfonyl)oxy)-1-naphthoate and other raw materials, reagents and preparation method were identical with those in step 2 of example 1 to give methyl 5-chloro-6-(4,4,5,5-tetramethyl-1,3,2-dioxaborolan-2-yl)-1-naphthoate as yellow solid.

$^1$H NMR (300 MHz, CDCl$_3$) δ (ppm): 1.43 (s, 12H), 4.00 (s, 3H), 7.60 (t, J=8.1 Hz, 1H), 7.79 (d, J=9.0 Hz, 1H), 8.23 (d, J=7.9H, 1H), 8.66 (d, r=8.4 Hz, 1H), 8.80 (d, J=8.7 Hz, 1H).

Step 4

5-chloro-6-(4,4,5,5-tetramethyl-1,3,2-dioxaborolan-2-yl)-1-naphthoic acid

Methyl 6-(4,4,5,5-tetramethyl-1,3,2-dioxaborolan-2-yl)-1-naphthoate was replaced by methyl 5-chloro-6-(4,4,5,5-tetramethyl-1,3,2-dioxaborolan-2-yl)-1-naphthoate and other raw materials, reagents and preparation method were identical with those in step 3 of example 1 to give 5-chloro-6-(4,4,5,5-tetramethyl-1,3,2-dioxaborolan-2-yl)-1-naphthoic acid as yellow solid.

Step 5

5-chloro-N-phenyl-6-(4,4,5,5-tetramethyl-1,3,2-dioxaborolan-2-yl)-1-naphthalenecarboxamide 6-(4,4,5,5-tetramethyl-1,3,2-dioxaborolan-2-yl)-1-naphthoic acid was replaced by 5-chloro-6-(4,4,5,5-tetramethyl-1,3,2-dioxaborolan-2-yl)-1-naphthoic acid and other raw materials, reagents and preparation method were identical with those in step 4 of example 1 to give 5-chloro-N-phenyl-6-(4,4,5,5-tetramethyl-1,3,2-dioxaborolan-2-yl)-1-naphthalene carboxamide as yellow solid.

Step 6

6-(3-amino-1H-indazol-4-yl)-5-fluoro-N-phenyl-1-naphthalenecarboxamide (I-32)

N-phenyl-6-(4,4, 5,5-tetramethyl-1,3,2-dioxaborolan-2-yl)-1-naphthalenecarboxamide was replaced by 5-chloro-N-phenyl-6-(4,4,5,5-tetramethyl-1,3,2-dioxaborolan-2-yl)-1-naphthalene carboxamide and other raw materials, reagents and preparation method were identical with those in step 6 of example 1 to give brown solid I-32.

$^1$H NMR (300 MHz, DMSO-d$_6$) δ (ppm): 4.01 (s, 2H), 6.84-6.86 (m, 1H), 7.14 (t, J=7.5 Hz, 1H), 7.35-7.42 (m, 4H), 7.63 (d, J=8.7 Hz, 1H), 7.82-7.89 (m, 3H), 7.92-7.94 (m, 1H), 8.25 (d, J=7.8 Hz, 1H), 8.49 (d, J=8.1 Hz, 1H), 10.72 (s, 1H), 11.80 (s, 1H).

EXAMPLE 33

6-(3-amino-7-fluoro-1H-indazol-4-yl)-N-phenyl-1-naphthalenecarboxamide (I-33)

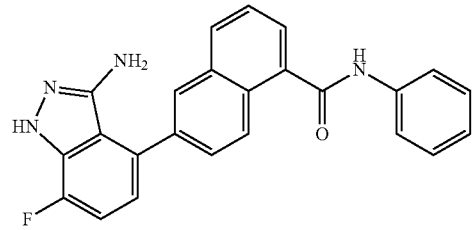

Step 1

7-fluoro-4-iodo-1H-indazol-3-amine 2-fluoro-6-iodobenzonitrile was replaced by 2,3-difluoro-6-iodobenzonitrile and other raw materials, reagents and preparation method were identical with those in step 5 of example 1 to give 7-fluoro-4-iodo-1H-indazol-3-amine as yellow solid.

$^1$H NMR (300 MHz, DMSO-d$_6$) δ (ppm): 5.18 (s, 2H), 6.88 (dd, J=11.1, 7.8 Hz, 1H), 7.28 (dd, J=8.1, 4.2 Hz, 1H), 12.33 (s, 1H).

Step 2

6-(3-amino-7-fluoro-1H-indazol-4-yl)-N-phenyl-1-naphthalenecarboxamide (I-33)

4-iodo-1H-indazol-3-amine was replaced by 7-fluoro-4-iodo-1H-indazol-3-amine and other raw materials, reagents and preparation method were identical with those in step 6 of example 1 to give white solid I-33.

$^1$H NMR (300 MHz, DMSO-d$_6$) δ (ppm): 4.43 (s, 2H), 6.88-6.92 (m, 1H), 7.11-7.24 (m, 2H), 7.36-7.42 (m, 2H), 7.65-7.74 (m, 2H), 7.80-7.85 (m, 3H), 8.11 (s, 1H), 8.18 (d, J=8.1 Hz, 1H), 8.30 (d, J=8.7 Hz, 1H), 10.62 (s, 1H), 12.34 (s, 1H).

EXAMPLE 34

6-(3-amino-7-bromo-1H-indazol-4-yl)-N-phenyl-1-naphthalenecarb oxamide (I-34)

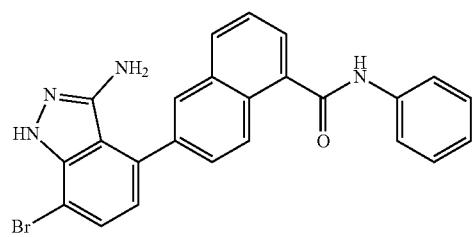 [SMILES: Nc1n[nH]c2c(F)ccc(-c3ccc4c(C(=O)Nc5ccccc5)cccc4c3)c12]

Step 1

7-bromo-4-iodo-1H-indazol-3-amine 2-fluoro-6-iodobenzonitrile was replaced by 3-bromo-2-fluoro-6-iodobenzonitrile and other raw materials, reagents and preparation method were identical with those in step 5 of example 1 to give 7-bromo-4-iodo-1H-indazol-3-amine as yellow solid.

$^1$H NMR (300 MHz, DMSO-$d_6$) δ (ppm): 5.18 (s, 2H), 7.19 (d, J=7.8 Hz, 1H), 7.27 (d, J=7.5 Hz, 1H), 12.18 (s, 1H).

Step 2

6-(3-amino-7-bromo-1H-indazol-4-yl)-N-phenyl-1-naphthalenecarboxamide (I-34)

4-iodo-1H-indazol-3-amine was replaced by 7-bromo-4-iodo-1H-indazol-3-amine and other raw materials, reagents and preparation method were identical with those in step 6 of example 1 to give white solid I-34.

$^1$H NMR (300 MHz, DMSO-$d_6$) δ (ppm): 4.45 (s, 2H), 6.89 (d, J=7.5 Hz, 1H), 7.14 (t, J=7.5 Hz, 1H), 7.37-7.42 (m, 2H), 7.59 (d, J=7.2 Hz, 1H), 7.69-7.75 (m, 2H), 7.81-7.85 (m, 3H), 8.15 (s, 1H), 8.19 (d, J=8.1 Hz, 1H), 8.32 (d, J=8.7 Hz, 1H), 10.64 (s, 1H), 12.22 (s, 1H).

EXAMPLE 35

6-(3-amino-7-methyl-1H-indazol-4-yl)-N-phenyl-1-naphthalenecarboxamide (I-35)

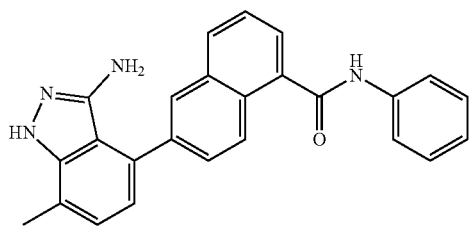 [SMILES: Cc1ccc(-c2ccc3c(C(=O)Nc4ccccc4)cccc3c2)c2c(N)n[nH]c12]

Step 1

4-iodo-7-methyl-1H-indazol-3-amine 2-fluoro-6-iodobenzonitrile was replaced by 2-fluoro-6-iodo-3-methylbenzonitrile and other raw materials, reagents and preparation method were identical with those in step 5 of example 1 to give 4-iodo-7-methyl-1H-indazol-3-amine as yellow solid.

$^1$H NMR (300 MHz, DMSO-$d_6$) δ (ppm): 2.33 (d, J=0.9 Hz, 3H), 5.02 (s, 2H), 6.74 (dd, J=7.5, 1.2 Hz, 1H), 7.24 (d, J=7.5 Hz, 1H), 11.83 (s, 1H).

Step 2

6-(3-amino-7-methyl-1H-indazol-4-yl)-N-phenyl-1-naphthalenecarboxamide (I-35)

4-iodo-1H-indazol-3-amine was replaced by 4-iodo-7-methyl-1H-indazol-3-amine and other raw materials, reagents and preparation method were identical with those in step 6 of example 1 to give white solid I-35.

$^1$H NMR (300 MHz, DMSO-$d_6$) δ (ppm): 2.47 (s, 3H), 4.31 (s, 2H), 6.86 (d, J=6.9 Hz, 1H), 7.11-7.16 (m, 2H), 7.39 (t, J=7.5 Hz, 2H), 7.64-7.69 (m, 1H), 7.72 (dd, J=8.4, 1.8 Hz, 1H), 7.78-7.80 (m, 1H), 7.84 (d, J=7.5 Hz, 2H), 8.10 (d, J=1.5 Hz, 1H), 8.17 (d, J=8.1 Hz, 1H), 8.29 (d, J=8.7 Hz, 1H), 10.63 (s, 1H), 11.88 (s, 1H).

EXAMPLE 36

6-(3-amino-1H-indazol-4-yl)-N-(3-methoxyphenyl)-1-naphthalenecarboxamide (I-36)

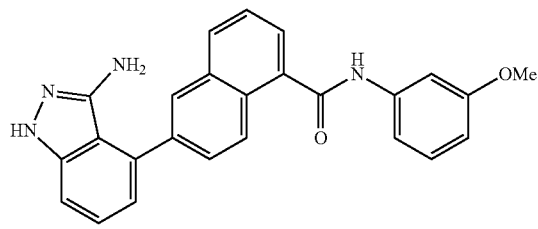

Step 1

N-(3-methoxyphenyl)-6-(4,4,5,5-tetramethyl-1,3,2-dioxaborolan-2-yl)-1-naphthalenecarboxamide Phenylamine was replaced by m-methoxyphenylamine and other raw materials, reagents and preparation method were identical with those in step 4 of example 1 to give N-(3-methoxyphenyl)-6-(4,4,5,5-tetramethyl-1,3,2-dioxaborolan-2-yl)-1-naphthalenecarboxamide as brown solid.

Step 2

6-(3-amino-1H-indazol-4-yl)-N-(3-methoxyphenyl)-1-naphthalenecarboxamide (I-36)

N-phenyl-6-(4,4,5,5-tetramethyl-1,3,2-dioxaborolan-2-yl)-1-naphthalenecarboxamide was replaced by N-(3-methoxyphenyl)-6-(4,4,5,5-tetramethyl-1,3,2-dioxaborolan-2-yl)-1-naphthalenecarboxamide and other raw materials, reagents and preparation method were identical with those in step 6 of example 1 to give white solid I-36.

$^1$H NMR (300 MHz, DMSO-$d_6$) δ (ppm): 3.77 (s, 3H), 4.31 (s, 2H), 6.72 (dd, J=8.1, 2.4 Hz, 1H), 6.94 (t, J=3.9 Hz, 1H), 7.26-7.31 (m, 1H), 7.34-7.35 (m, 2H), 7.39 (d, J=8.4 Hz, 1H), 7.55 (s, 1H), 7.65-7.70 (m, 1H), 7.75 (dd, J=8.7, 1.5 Hz, 1H), 7.79 (d, J=7.2 Hz, 1H), 8.13 (d, J=1.5 Hz, 1H), 8.19 (d, J=8.7 Hz, 1H), 8.29 (d, J=8.7 Hz, 1H), 10.61 (s, 1H), 11.83 (s, 1H).

EXAMPLE 37

6-(3-amino-1H-indazol-4-yl)-N-(3-(trifluoromethoxy)phenyl)-1-naphthalene-carboxamide (I-37)

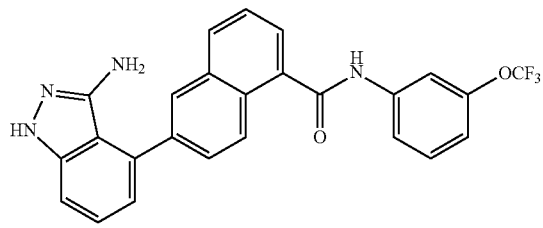 [SMILES: Nc1n[nH]c2cccc(-c3ccc4c(C(=O)Nc5cccc(OC(F)(F)F)c5)cccc4c3)c12]

Step 1

N-(3-trifluoromethoxyphenyl)-6-(4,4,5,5-tetramethyl-1,3,2-dioxaborolan-2-yl)-1-naphthalenecarboxamide Phenylamine was replaced by m-trifluoromethoxyphenyl amine and other raw materials, reagents and preparation method were identical with those in step 4 of example 1 to give N-(3-trifluoromethoxyphenyl)-6-(4,4, 5, 5-tetramethyl-1,3,2-dioxaborolan-2-yl)-1-naphthalenecarboxamide as brown solid.

$^1$H NMR (300 MHz, CDCl$_3$) δ (ppm): 1.40 (s, 12H), 7.05 (dd, J=8.4, 0.9 Hz, 1H), 7.38-7.43 (m, 1H), 7.49-7.55 (m, 2H), 7.75-7.79 (m, 3H), 7.93 (dd, J=8.4, 1.2 Hz, 1H), 8.03 (d, J=8.1 Hz, 1H), 8.32 (d, J=8.7 Hz, 1H), 8.42 (s, 1H).

Step 2

6-(3-amino-1H-indazol-4-yl)-N-(3-(tri fluoromethoxy)phenyl)-1-naphthalenecarboxamide (I-37)

N-phenyl-6-(4,4,5,5-tetramethyl-1,3,2-dioxaborolan-2-yl)-1-naphthalenecarboxamide was replaced by N-(3-trifluoromethoxyphenyl)-6-(4,4, 5,5-tetramethyl-1,3,2-dioxaborolan-2-yl)-1-naphthalenecarboxamide and other raw materials, reagents and preparation method were identical with those in step 6 of example 1 to give white solid I-37.

$^1$H NMR (300 MHz, DMSO-d$_6$) δ (ppm): 4.31 (s, 2H), 6.93-6.96 (m, 1H), 7.12-7.15 (m, 1H), 7.34-7.36 (m, 2H), 7.52 (t, J=8.1 Hz, 1H), 7.69 (dd, J=8.1, 7.2 Hz, 1H), 7.74-7.77 (m, 2H), 7.86 (dd, J=7.2, 0.9 Hz, 1H), 8.03 (s, 1H), 8.14 (d, J=1.5 Hz, 1H), 8.21 (d, J=8.4 Hz, 1H), 8.32 (d, J=8.7 Hz, 1H), 10.92 (s, 1H), 11.83 (s, 1H).

EXAMPLE 38

6-(3-amino-1H-indazol-4-yl)-N-(3-hydroxyphenyl)-1-naphthalenecarboxamide (I-38)

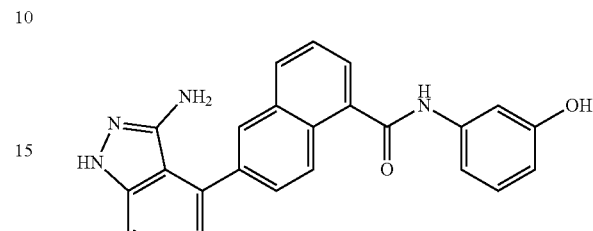

Step 1

N-(3-hydroxyphenyl)-6-(4,4,5,5-tetramethyl-1,3,2-dioxaborolan-2-yl)-1-naphthalenecarboxamide Phenylamine was replaced by m-hydroxyphenylamine and other raw materials, reagents and preparation method were identical with those in step 4 of example 1 to give N-(3-hydroxyphenyl)-6-(4,4,5,5-tetramethyl-1,3,2-dioxaborolan-2-yl)-1-naphthalenecarboxamide as brown solid.

Step 2

6-(3-amino-1H-indazol-4-yl)-N-(3-(tri fluoromethoxy)phenyl)-1-naphthalenecarboxamide (I-38)

N-phenyl-6-(4,4,5,5-tetramethyl-1,3,2-dioxaborolan-2-yl)-1-naphthalene carb oxamide was replaced by N-(3-hydroxyphenyl)-6-(4,4,5,5-tetramethyl-1,3,2-dioxaborolan-2-yl)-1-naphthalenecarboxamide and other raw materials, reagents and preparation method were identical with those in step 6 of example 1 to give white solid I-38.

$^1$H NMR (300 MHz, DMSO-d$_6$) δ (ppm): 6.52-6.56 (m, 1H), 6.97 (dd, J=4.2, 3.6 Hz, 1H), 7.12-7.20 (m, 2H), 7.37-7.38 (m, 2H), 7.42 (s, 1H), 7.63-7.69 (m, 1H), 7.72-7.77 (m, 2H), 8.12 (d, J=1.5 Hz, 1H), 8.17 (d, J=8.1 Hz, 1H), 8.27 (d, J=8.7 Hz, 1H), 10.51 (s, 1H).

EXAMPLE 39

6-(3-amino-1H-indazol-4-yl)-N-(3-nitrophenyl)-1-naphthalenecarboxamide (I-39)

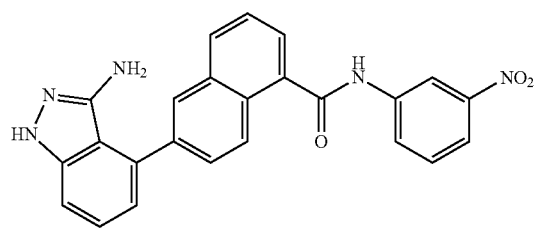 [SMILES: Nc1n[nH]c2cccc(-c3ccc4c(C(=O)Nc5cccc([N+](=O)[O-])c5)cccc4c3)c12]

Step 1

N-(3-nitrophenyl)-6-(4,4,5,5-tetramethyl-1,3,2-dioxaborolan-2-yl)-1-naphthalenecarboxamide Phenylamine was replaced by m-nitrophenylamine and other raw materials, reagents and preparation method were identical with those in step 4 of example 1 to give N-(3-nitrophenyl)-6-(4,4,5,5-tetramethyl-1,3,2-dioxaborolan-2-yl)-1-naphthalenecarboxamide as brown solid.

Step 2

6-(3-amino-1H-indazol-4-yl)-N-(3-nitrophenyl)-1-naphthalenecarboxamide (I-39)

N-phenyl-6-(4,4,5,5-tetramethyl-1,3,2-dioxaborolan-2-yl)-1-naphthalenecarboxamide was replaced by N-(3-nitrophenyl)-6-(4,4,5,5-tetramethyl-1,3,2-dioxaborolan-2-yl)-1-naphthalenecarboxamide and other raw materials, reagents and preparation method were identical with those in step 6 of example 1 to give white solid I-39.

$^1$H NMR (300 MHz, DMSO-$d_6$) δ (ppm): 4.33 (s, 2H), 6.95 (t, J=3.9 Hz, 1H), 7.34-7.36 (m, 2H), 7.67-7.78 (m, 3H), 7.88 (d, J=6.9 Hz, 1H), 8.02 (dd, J=8.1, 1.5 Hz, 1H), 8.15-8.18 (m, 2H), 8.23 (d, J=8.1 Hz, 1H), 8.35 (d, J=8.7 Hz, 1H), 8.91 (s, 1H), 11.12 (s, 1H), 11.84 (s, 1H).

EXAMPLE 40

6-(3-amino-1H-indazol-4-yl)-N-(3-aminophenyl)-1-naphthalenecarboxamide (I-40)

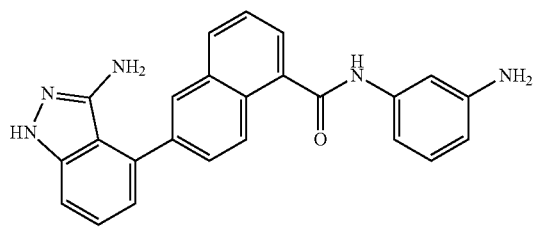

20 mg of 6-(3-amino-1H-indazol-4-yl)-N-(3-nitrophenyl)-1-naphthalenecarboxamide (I-39) was dissloved in 1 ml of ethanol, 25 mg of ammonium chloride in 0.5 ml water and 13 mg of iron powder were added and heated to 70° C. After stirred for 0.5 h, the mixture was cooled to room temperature, filtered and then concentrated. Water and ethyl acetate were added to separate. The aqueous phase was extracted with ethyl acetate. The combined organic phases was washed with saturated sodium chloride, dried over anhydrous sodium sulfate, filtered and concentrated to give 13 mg of white solid I-40. Yield: 72%.

$^1$H NMR (300 MHz, DMSO-$d_6$) δ (ppm): 4.31 (s, 2H), 5.16 (s, 2H), 6.34 (dd, J=7.8, 0.9 Hz, 1H), 6.88 (d, J=8.1 Hz, 1H), 6.93-7.01 (m, 2H), 7.21 (s, 1H), 7.34-7.35 (m, 2H), 7.63-7.68 (m, 1H), 7.72-7.75 (m, 2H), 8.11 (d, J=1.5 Hz, 1H), 8.16 (d, J=8.1 Hz, 1H), 8.27 (d, J=9.0 Hz, 1H), 10.33 (s, 1H), 11.84 (s, 1H).

EXAMPLE 41

6-(3-aminobenzo[d]isoxazol-4-yl)-N-phenyl-1-naphthalenecarboxamide (I-41)

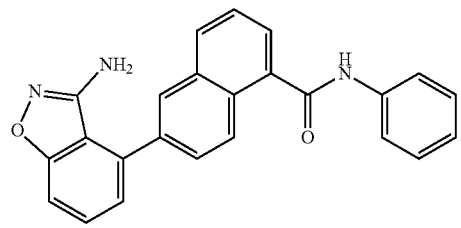 [SMILES: Nc1noc2cccc(-c3ccc4c(C(=O)Nc5ccccc5)cccc4c3)c12]

Step 1

4-iodobenzo[d]isoxazol-3-amine 61 mg of acetohydroxamic acid was dissloved in 1 ml of N,N-dimethylformamide and 91 mg of potassium t-butoxide was added slowly with stirring and stirred for 0.5 h at room temperature. Then 100 mg of 2-fluoro-6-iodobenzonitrile was added slowly and stirred for 12 hours at room temperature. Then 10 ml of water was added and the mixture was filtered. The filter cake was washed with water and dried to give 72 mg of 4-iodobenzo[d]isoxazol-3-amine as white solid. Yield: 69%.

$^1$H NMR (300 MHz, DMSO-$d_6$) δ (ppm): 5.93 (s, 2H), 7.24-7.29 (m, 1H), 7.55 (dd, J=8.4, 0.6 Hz, 1H), 7.69-7.71 (m, 1H).

Step 2

6-(3-aminobenzo[d]isoxazol-4-yl)-N-phenyl-1-naphthalenecarboxamide (I-41)

4-iodo-1H-indazol-3-amine was replaced by 4-iodobenzo[d]isoxazol-3-amine and other raw materials, reagents and preparation method were identical with those in step 6 of example 1 to give white solid I-41.

$^1$H NMR (300 MHz, DMSO-$d_6$) δ (ppm): 5.23 (s, 2H), 7.14 (t, J=7.5 Hz, 1H), 7.30 (dd, J=7.2, 0.9 Hz, 1H), 7.37-7.42 (m, 2H), 7.59 (dd, J=8.1, 0.6 Hz, 1H), 7.64-7.72 (m, 2H), 7.77 (dd, J=8.4, 1.5 Hz, 1H), 7.83-7.85 (m, 3H), 8.19-8.21 (m, 2H), 8.35 (d, J=8.7 Hz, 1H), 10.63 (s, 1H).

EXAMPLE 42

6-(3-amino-7-fluorobenzo[d]isoxazol-4-yl)-N-phenyl-1-naphthalenecarboxamide (I-42)

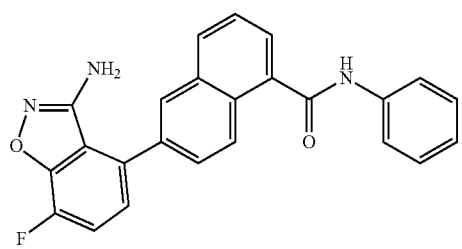 [SMILES: Nc1noc2c(F)ccc(-c3ccc4c(C(=O)Nc5ccccc5)cccc4c3)c12]

Step 1

7-fluoro-4-iodobenzo[d]isoxazol-3-amine 2-fluoro-6-iodobenzonitrile was replaced by 2,3-difluoro-6-iodobenzonitrile and other raw materials, reagents and preparation method were identical with those in step 1 of example 41 to give 7-fluoro-4-iodobenzo[d]isoxazol-3-amine as white solid.

Step 2

6-(3-amino-7-fluorobenzo[d]isoxazol-4-yl)-N-phenyl-1-naphthalenecarboxamide (I-42)

4-iodo-1H-indazol-3-amine was replaced by 7-fluoro-4-iodobenzo[d]isoxazol-3-amine and other raw materials, reagents and preparation method were identical with those in step 6 of example 1 to give yellow solid I-42.

$^1$H NMR (300 MHz, DMSO-$d_6$) δ (ppm): 5.41 (s, 2H), 7.11-7.16 (m, 1H), 7.26-7.30 (m, 1H), 7.39 (t, J=7.5 Hz, 2H), 7.58-7.76 (m, 3H), 7.82-7.85 (m, 3H), 8.18-8.20 (m, 2H), 8.35 (d, J=8.7 Hz, 1H), 10.63 (s, 1H).

EXAMPLE 43

6-(3-amino-7-methylbenzo[d]isoxazol-4-yl)-N-phenyl-1-naphthalenecarboxamide (I-43)

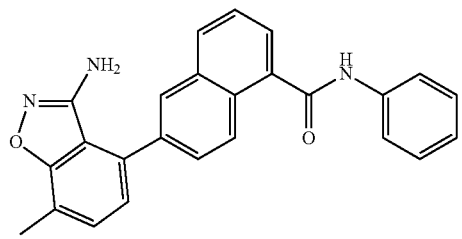 [SMILES: Cc1ccc(-c2ccc3c(C(=O)Nc4ccccc4)cccc3c2)c2c(N)noc12]

Step 1

4-iodo-7-methylbenzo[d]isoxazol-3-amine 2-fluoro-6-iodobenzonitrile was replaced by 2-fluoro-6-iodo-3-methylbenzonitrile and other raw materials, reagents and preparation method were identical with those in step 1 of example 41 to give 4-iodo-7-methylbenzo[d]isoxazol-3-amine as white solid.

$^1$H NMR (300 MHz, DMSO-$d_6$) δ (ppm): 2.35 (s, 3H), 5.91 (s, 2H), 7.09 (dd, J=7.5, 0.9 Hz, 1H), 7.58 (d, J=7.2 Hz, 1H).

Step 2

6-(3-amino-7-methylbenzo[d]isoxazol-4-yl)-N-phenyl-1-naphthalenecarboxamide (I-43)

4-iodo-1H-indazol-3-amine was replaced by 4-iodo-7-methylbenzo[d]isoxazol-3-amine and other raw materials, reagents and preparation method were identical with those in step 6 of example 1 to give white solid I-43.

$^1$H NMR (300 MHz, DMSO-$d_6$) δ (ppm): 5.22 (s, 2H), 7.14 (t, J=7.5 Hz, 1H), 7.20 (d, J=7.5 Hz, 1H), 7.40 (t, J=8.1 Hz, 2H), 7.48 (d, J=7.5 Hz, 1H), 7.67-7.76 (m, 2H), 7.83-7.85 (m, 3H), 8.16-8.21 (m, 2H), 8.34 (d, J=8.7 Hz, 1H), 10.63 (s, 1H).

EXAMPLE 44

6-(3-amino-7-methoxybenzo[d]isoxazol-4-yl)-N-phenyl-1-naphthalenecarboxamide (I-44)

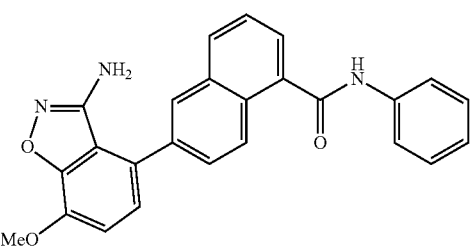 [SMILES: COc1ccc(-c2ccc3c(C(=O)Nc4ccccc4)cccc3c2)c2c(N)noc12]

Step 1

4-iodo-7-methoxybenzo[d]isoxazol-3-amine 2-fluoro-6-iodobenzonitrile was replaced by 2-fluoro-6-iodo-3-methoxybenzonitrile and other raw materials, reagents and preparation method were identical with those in step 1 of example 41 to give 4-iodo-7-methoxybenzo[d]isoxazol-3-amine as white solid.

$^1$H NMR (300 MHz, DMSO-$d_6$) δ (ppm): 3.91 (s, 3H), 5.91 (s, 2H), 6.91 (d, J=8.4 Hz, 1H), 7.57 (d, J=8.1 Hz, 1H).

Step 2

6-(3-amino-7-methoxybenzo[d]isoxazol-4-yl)-N-phenyl-1-naphthalenecarboxamide (I-44)

4-iodo-1H-indazol-3-amine was replaced by 4-iodo-7-methoxybenzo[d]isoxazol-3-amine and other raw materials, reagents and preparation method were identical with those in step 6 of example 1 to give white solid I-44.

$^1$H NMR (300 MHz, DMSO-$d_6$) δ (ppm): 4.00 (s, 3H), 5.23 (s, 2H), 7.14 (t, J=7.5 Hz, 1H), 7.20-7.26 (m, 2H), 7.39 (t, J=7.5 Hz, 2H), 7.65-7.74 (m, 2H), 7.81-7.85 (m, 3H), 8.13 (s, 1H), 8.18 (d, J=8.4 Hz, 1H), 8.32 (d, J=8.4 Hz, 1H), 10.61 (s, 1H).

EXAMPLE 45

Effect of the Compound on the Activity of VEGFR-2 at Molecular Level

1. Experimental Method

The enzyme reaction substrate Poly(Glu, Tyr)4:1 was diluted with potassium-free PBS (10 mM sodium phosphate buffer, 150 mM NaCl, pH 7.2-7.4) to 20 μg/ml and microwell plate was coated with 125 ml/well mixture. The reaction was carried out at 37° C. for 12-16 h. Then the liquid was discarded and the microwell plate was washed with 200 ml/well T-PBS (PBS containing 0.1% Tween-20) three times, 5 minutes each. The microwell plate was dried for 1-2 hours at 37° C. oven. Each well was added with reaction buffer (50 mM HEPES, pH 7.4, 50 mM $MgCl_2$, 5 mM $MnCl_2$, 0.2 mM $Na_3VO_4$, 1 mM DTT) diluted ATP solution (50 mL) whose final concentration is 5 μM. Drug was diluted with 1% DMSO to a suitable concentration. 10 µl/well of drug was added and then 40 µl reaction buffer diluted VEGFR-2 tyrosine kinase protein was added. The microwell plate was placed into a shaker (100 rpm) and the reaction was carried out at 37° C. for 1 h. The microwell plate was washed with T-PBS three times. Three enzyme-free control wells and corresponding concentration of DMSO control wells were required for each experiment. 100 ml of primary antibody PY99 (p-Tyr (PY99), Cell Signaling Technology, diluted with T-PBS containing 5 mg/ml BSA, 1:1000 dilution) was added to each well and the plate was placed into a shaker to react for 0.5 h at 37° C. The plate was washed with T-PBS three times. 100 ml of secondary antibody horseradish peroxidase-labeled goat anti-mouse IgG (diluted with T-PBS containing 5 mg/ml BSA, 1:2000 dilution) was added to each well and the plate was placed into a shaker to react for 0.5 h at 37° C. The plate was washed with T-PBS three times. 100 ml of 2 mg/ml of OPD developing solution (diluted with 0.1 M citric acid-sodium citrate buffer containing 0.03% of $H_2O_2$ (pH=5.4)) was added to each well and the reaction was carried out at 25° C. in the dark for 1-10 minutes. OPD was dissolved under ultrasound and developing solution was freshly prepared. 50 ml of 2 M $H_2SO_4$ was added to each well to quench the reaction and OD value was measured by wavelength tunable microplate reader SPECTRA MAX 190. Wavelength was 490 nm.

Inhibition rate of the compound was obtained by the following formula:

$$\text{Inhibition rate of the compound \%} = \frac{\text{Average } OD \text{ value of negative control group} - \text{Average } OD \text{ value of compound group}}{\text{Average } OD \text{ value of negative control group}} \times 100\%$$

$IC_{50}$ values were calculated by inhibition curves with four parameters fitting.

2. Experimental Results

Enzyme activity assay at molecular level showed that naphthylamide compounds of the present invention at nanomolar concentration have good inhibitory effect on VEGFR-2 tyrosine kinase. Half VEGFR-2 inhibitory concentration of some compounds was about 1 nM and better than positive control compounds SU11248 and ABT869. The compounds of the present invention were potent VEGFR-2 tyrosine kinase inhibitors.

TABLE 2

Half inhibitory concentration of compounds in examples of the preset invention for receptor tyrosine kinase VEGFR-2

| Compound | $IC_{50}$ (nM) |
|---|---|
| SU11248[a] | 7.4 |
| ABT869[b] | 6.2 |
| I-1 | 1.6 |
| I-2 | 7.0 |
| I-3 | 7.1 |
| I-4 | 1.5 |
| I-5 | 1.3 |
| I-6 | 26.7 |
| I-7 | 7.3 |
| I-8 | 1.9 |
| I-9 | 18.2 |
| I-10 | 18.7 |
| I-11 | 7.1 |
| I-12 | 9.2 |
| I-13 | 92.5 |

TABLE 2-continued

Half inhibitory concentration of compounds in examples of the preset invention for receptor tyrosine kinase VEGFR-2

| Compound | $IC_{50}$ (nM) |
|---|---|
| I-14 | 10.8 |
| I-15 | 48.4 |
| I-16 | 24.0 |
| I-17 | 1.4 |
| I-18 | 2.5 |
| I-19 | 7.3 |
| I-20 | 3.8 |
| I-21 | 8.1 |
| I-22 | 7.6 |
| I-23 | 4.5 |
| I-24 | 9.7 |
| I-25 | 20.2 |
| I-26 | 101.3 |
| I-27 | 95.2 |
| I-28 | 8.6 |

[a]SU11248, positive control (Mendel, D. B. et al., *Clin. Cancer Res.* 2003; 9 (1): 327-37.)
[b]ABT869, positive control (Dai, Y. et al., *J. Med. Chem.* 2007; 50 (7): 1584-97.)

EXAMPLE 46

Effect of Compound at Cellular Level on VEGF-Induced Human Umbilical Vein Endothelial Cells (HUVEC) Proliferation 1. Experimental Method 5000-8000 primary HUVEC cells before 5-15 doublings were seeded to each well of 96-well plate and each well contained 90 µl. The cells were cultured overnight and then starved with 90 µl/well serum-free basal culture medium for 24 h. Then 10 µl different concentration of compound was added to each well. Five concentrations were set and each concentration had 3 wells. After 2 h, 100 ng/mL of VEGF growth-stimulating factor was added. After 48 h, the medium was discarded, the cells were fixed with pre-cooled 10% TCA at 4° C. for 1 h, then washed with distilled water five times and dried in air. Then 100 µl of 4 mg/ml of sulforodamine B (SRB) solution prepared from 1% acetic acid was added to each well to dye 15 minutes at room temperature. The staining solution was discarded and each well was washed with 1% acetic acid five times and then dried in air. Finally, each well was added with 150 µl Tris-HCl solution (10 mM Tris, pH 10.0) and absorbance OD values at 560 nm were measured by microplate reader. Inhibition rate of the compound on HUVEC cell proliferation was measured to reflect VEGF-mediated proliferation inhibition effect of compound.

Inhibition rate of the compound was obtained by the following formula:

$$\text{Inhibition rate of the compound \%} = \frac{\text{Average } OD \text{ value of negative control group} - \text{Average } OD \text{ value of compound group}}{\text{Average } OD \text{ value of negative control group}} \times 100\%$$

$IC_{50}$ values were calculated by inhibition curves with four parameters fitting.

2. Experimental Results

It can be seen from the data in table 3 that half inhibitory concentrations of most of naphthylamide compounds of the present invention for VEGF-induced human umbilical vein endothelial cells (HUVEC) proliferation were in the nanomolar level, wherein cell activities of compounds I-4, I-8, I-9, I-14 and I-21 were stronger than that of positive control compound ABT869.

TABLE 3

Half inhibitory concentrations of compounds in examples of the present invention for VEGF-induced human umbilical vein endothelial cells (HUVEC) proliferation

| Compound in the example | IC$_{50}$ (nM) |
|---|---|
| ABT869 | 2.32 |
| I-1 | 3.76 |
| I-2 | 20.54 |
| I-3 | 20.17 |
| I-4 | 0.9 |
| I-6 | 86.36 |
| I-7 | 2.08 |
| I-8 | 1.3 |
| I-9 | 1.44 |
| I-10 | 6.1 |
| I-11 | 2.26 |
| I-12 | 16.99 |
| I-13 | 2.63 |
| I-14 | 1.57 |
| I-15 | 3.12 |
| I-16 | 3.86 |
| I-17 | >100 |
| I-18 | >100 |
| I-19 | >100 |
| I-20 | 6.09 |
| I-21 | 1.53 |
| I-22 | 3.261 |
| I-23 | 4.456 |
| I-24 | 5.72 |
| I-26 | 6.96 |
| I-27 | 2.79 |

The invention claimed is:

1. A compound of formula (II), or a pharmaceutically acceptable salt, prodrug, hydrate, or solvate thereof:

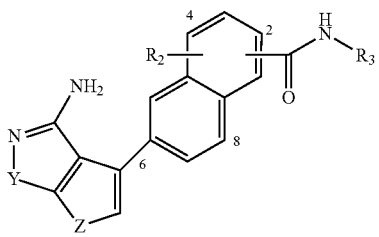

wherein:
$R_2$ is hydrogen or halogen, and $R_2$ is located at any one of positions 1-5 and 7-8 on the naphthalene ring, provided that $R_2$ is not located at the same position as

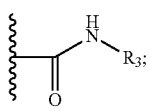

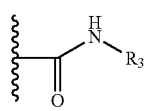

is located at any one of positions 1-4 on the naphthalene ring;

$R_3$ is selected from the group consisting of hydrogen, C1-C6 alkyl, C3-C6 cycloalkyl, a substituted or unsubstituted phenyl, and a substituted or unsubstituted 5-10 membered heteroaryl containing 1-5 hetero atoms selected from the group consisting of N, O and S; when the phenyl or heteroaryl is substituted, the substituent is 1 to 3 substituents and each substituent is independently selected from the group consisting of C1-C3 alkyl, C1-C3 alkoxy, C1-C3 haloalkyl, C1-C3 haloalkoxy, hydroxy, amino, nitro, and halogen;

Z is $C(R_5)$=CH, S or O;

Y is NH, NMe, O, CH=C($R_6$) or CH=N;

$R_5$ is selected from the group consisting of hydrogen, halogen, C1-C3 alkyl, and C1-C3 alkoxy; and $R_6$ is selected from the group consisting of hydrogen, pyrazolyl, C1-C3 alkyl-substituted pyrazolyl, and C1-C3 hydroxyalkyl-substituted pyrazolyl.

2. The compound of claim 1, being a compound of formula (III), (IV), (V) or (VI), or pharmaceutically acceptable salt, prodrug, hydrate, or solvate thereof:

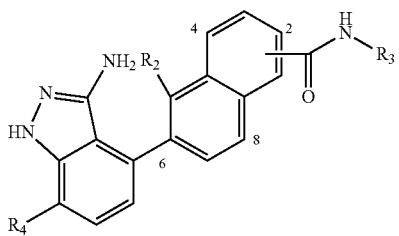

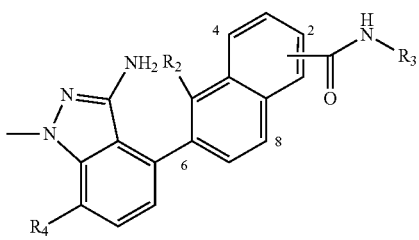

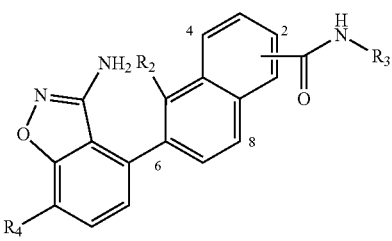

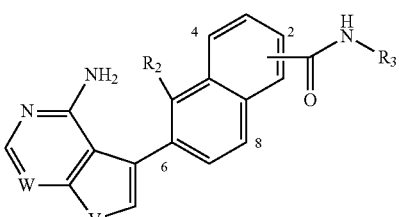

wherein

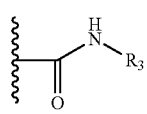

is located at position 1 or 2 on the naphthalene ring;

R₂ and R₃ are defined as described in claim 1;

R₄ is selected from the group consisting of hydrogen, halogen, C1-C3 alkyl, and C1-C3 alkoxy;

V is S or O;

W is N or C(R₇); and

R₇ is selected from the group consisting of hydrogen, pyrazolyl, C1-C3 alkyl-substituted pyrazolyl, and C1-C3 hydroxyalkyl-substituted pyrazolyl.

3. A compound selected from the group consisting of:

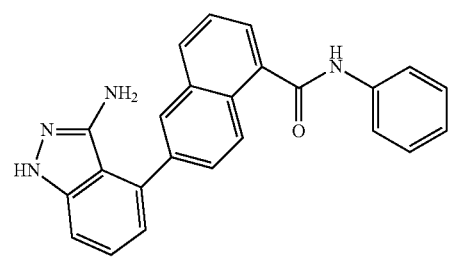

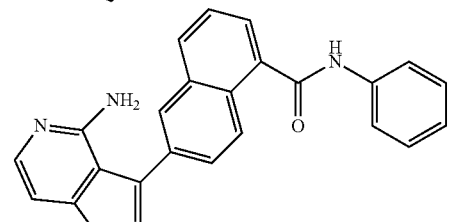

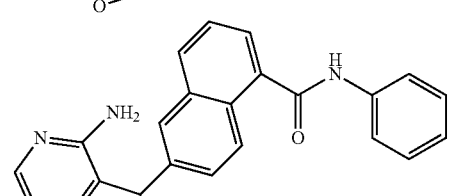

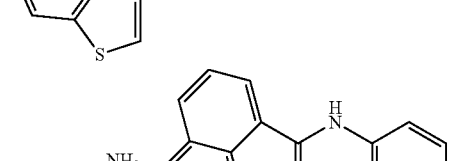

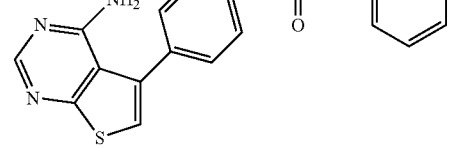

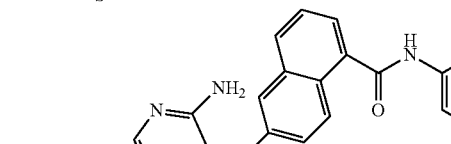

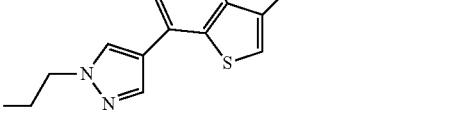

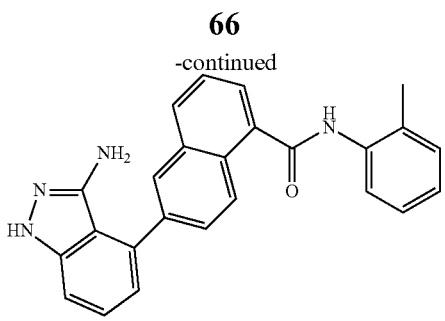

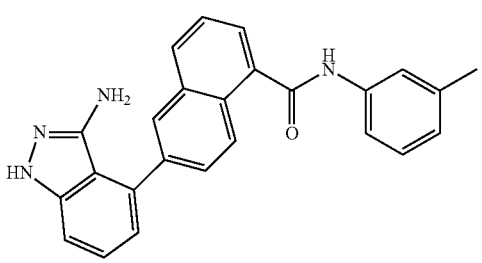

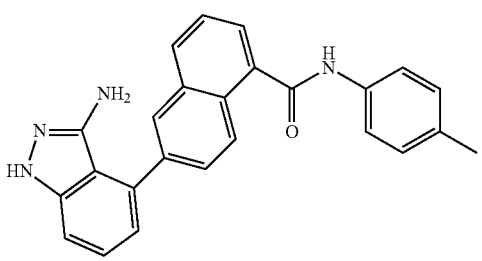

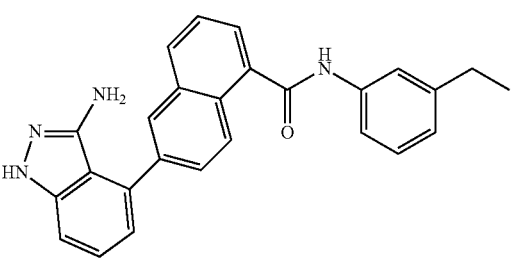

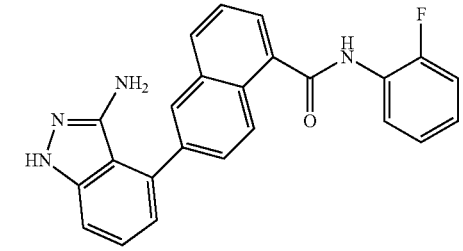

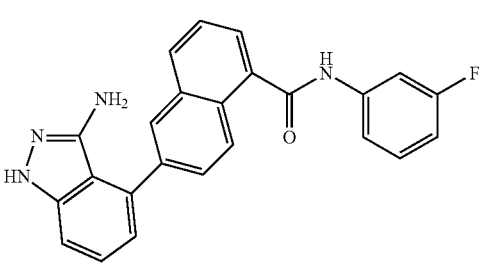

-continued

-continued

-continued

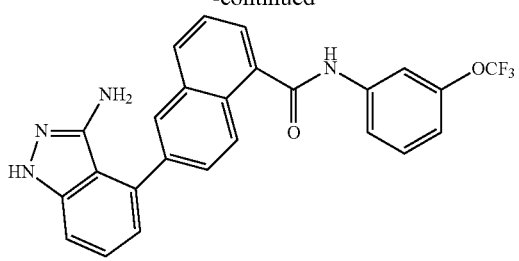
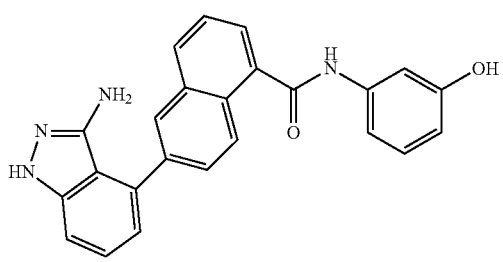
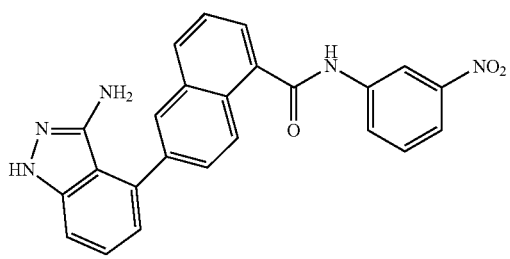
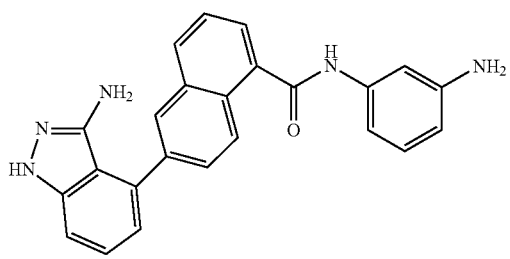
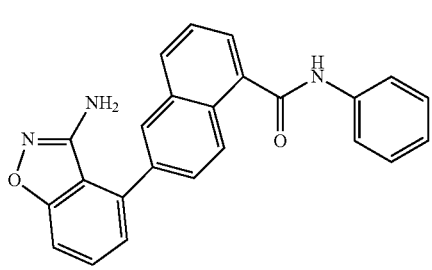
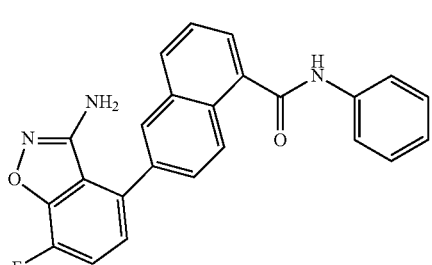

-continued

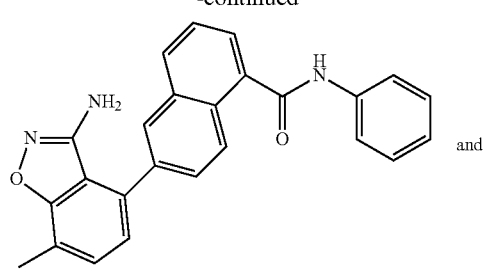

and

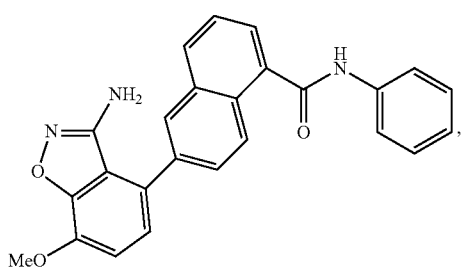

, or a pharmaceutically acceptable salt, prodrug, hydrate, or solvate thereof.

4. A pharmaceutical composition comprising a therapeutically effective amount of at least one compound of claim 1, and optionally a pharmaceutically acceptable carrier.

5. The compound of claim 1, wherein:

the group

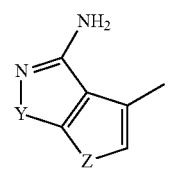

at position 6 of the naphthalene ring is selected from the group consisting of:

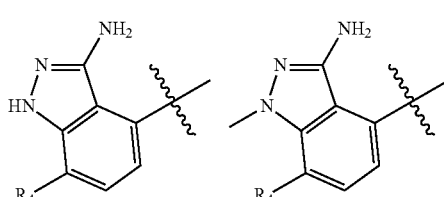
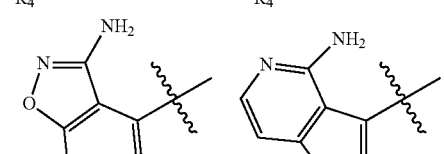
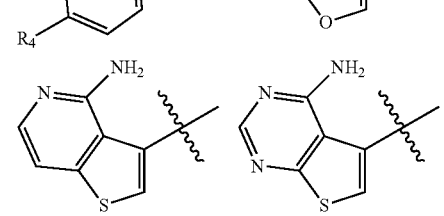
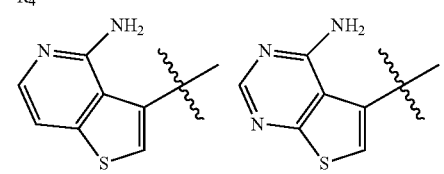

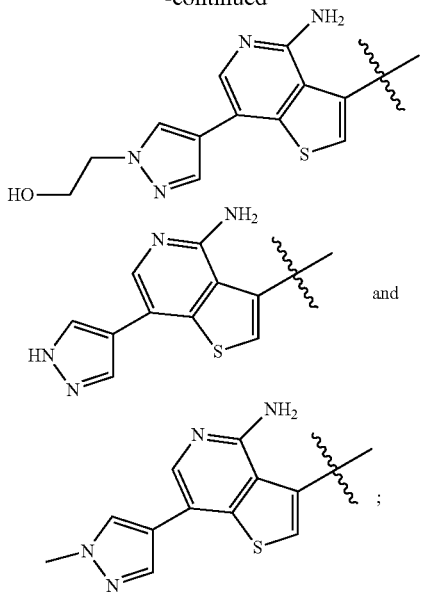

and

R$_4$ is selected from the group consisting of hydrogen, halogen, C1-C3 alkyl and C1-C3 alkoxy.

6. The compound of claim 1, wherein R$_5$ is selected from the group consisting of hydrogen, F, Cl, Br, methyl, and methoxy.

7. The compound of claim 1, wherein R$_6$ is selected from the group consisting of hydrogen, pyrazolyl, methyl-substituted pyrazolyl, and hydroxyethyl-substituted pyrazolyl.

8. The compound of formula (II) of claim 2, wherein R$_7$ is selected from the group consisting of hydrogen, pyrazolyl, methyl-substituted pyrazolyl, and hydroxyethyl-substituted pyrazolyl.

9. A pharmaceutical composition comprising a therapeutically effective amount of at least one compound of claim 3, and optionally a pharmaceutically acceptable carrier.

10. A method for treating a disease related to abnormal angiogenesis in a subject in need thereof, the method comprising administering to the subject the pharmaceutical composition of claim 4, wherein the disease related to abnormal angiogenesis is characterized by overexpression of VEGFR-2.

11. The method of claim 10, wherein the disease related to abnormal angiogenesis is selected from the group consisting of tumor, rheumatoid arthritis, age-related macular degeneration, and psoriasis.

12. The method of claim 11, wherein the tumor is selected from the group consisting of lung cancer, breast cancer, colon cancer, prostate cancer, stomach cancer, liver cancer, ovarian cancer, renal cancer, glioma, melanoma, pancreatic cancer, head and neck cancer, bladder cancer, cervical cancer, cholangiocarcinoma, nasopharyngeal cancer, thyroid cancer, osteosarcoma, synovial sarcoma, rhabdomyosarcoma, fibrosarcoma, leiomyosarcoma, myeloma, and lymphoma.

13. A method of inhibiting a protein tyrosine kinase in a subject in need thereof, the method comprising administering to the subject the pharmaceutical composition of claim 4, wherein the protein tyrosine kinase is VEGFR-2.

14. A method of treating a disease related to abnormal angiogenesis in a subject in need thereof, the method comprising administering to the subject the pharmaceutical composition of claim 9, wherein the disease related to abnormal angiogenesis is characterized by overexpression of VEGFR-2.

15. The method of claim 14, wherein the disease related to abnormal angiogenesis is selected from the group consisting of tumor, rheumatoid arthritis, age-related macular degeneration, and psoriasis.

16. The method of claim 15, wherein the tumor is selected from the group consisting of lung cancer, breast cancer, colon cancer, prostate cancer, stomach cancer, liver cancer, ovarian cancer, renal cancer, glioma, melanoma, pancreatic cancer, head and neck cancer, bladder cancer, cervical cancer, cholangiocarcinoma, nasopharyngeal cancer, thyroid cancer, osteosarcoma, synovial sarcoma, rhabdomyosarcoma, fibrosarcoma, leiomyosarcoma, myeloma, and lymphoma.

17. A method of inhibiting a protein tyrosine kinase in a subject in need thereof, the method comprising administering to the subject the pharmaceutical composition of claim 9, wherein the protein tyrosine kinase is VEGFR-2.

18. The method of claim 12, wherein the tumor is selected from the group consisting of glioma, lung cancer, breast cancer, renal cancer, ovarian cancer, and gastrointestinal cancer.

19. The method of claim 16, wherein the tumor is selected from the group consisting of glioma, lung cancer, breast cancer, renal cancer, ovarian cancer, and gastrointestinal cancer.

20. The method of claim 13, wherein the subject is in need of a treatment of a disease related to abnormal angiogenesis.

* * * * *